United States Patent [19]

Rosamond et al.

[11] Patent Number: 5,502,164
[45] Date of Patent: Mar. 26, 1996

[54] PEPTIDE COMPOUNDS HAVING THERAPEUTIC ACTIVITY

[75] Inventors: James D. Rosamond, Honeoye; Myles E. Pierson, Pittsford, both of N.Y.

[73] Assignee: Fisons Corporation, Rochester, N.Y.

[21] Appl. No.: 294,203

[22] Filed: Aug. 22, 1994

Related U.S. Application Data

[63] Continuation of Ser. No. 994,542, Dec. 21, 1992, abandoned, which is a continuation-in-part of Ser. No. 810,985, Dec. 20, 1991, abandoned, which is a continuation-in-part of PCT/US90/06739, Nov. 16, 1990, which is a continuation-in-part of Ser. No. 441,275, Nov. 27, 1989, abandoned.

[30] Foreign Application Priority Data

Sep. 29, 1992 [GB] United Kingdom ............ 9220543
Oct. 2, 1992 [GB] United Kingdom ............ 9220761

[51] Int. Cl.$^6$ .................... A61K 38/00; C07K 7/00; C07K 7/06
[52] U.S. Cl. .................... 530/329
[58] Field of Search ................ 530/327; 514/17

[56] References Cited

U.S. PATENT DOCUMENTS

| | | | |
|---|---|---|---|
| 4,490,364 | 12/1984 | Rivier et al. | 530/328 |
| 5,013,722 | 5/1991 | Danho et al. | 530/328 |
| 5,086,042 | 2/1992 | Rosamond | 530/327 |

FOREIGN PATENT DOCUMENTS

| | | |
|---|---|---|
| 0226217 | 6/1987 | European Pat. Off. . |
| 0268297 | 5/1988 | European Pat. Off. . |
| 0285061 | 10/1988 | European Pat. Off. . |
| 0381340 | 8/1990 | European Pat. Off. . |
| 1309464 | 3/1970 | United Kingdom . |
| 9108225 | 6/1991 | WIPO . |

OTHER PUBLICATIONS

American Journal of Physiology, vol. 258, 1990, Chun Wel Lin et al. "A71378: a CCK agonist with high potency and selectivity for CCK–A receptors" (Abstract, pG649, col. 2, 1. 1–13).

Journal of Medicinal Chemistry vol. 35, No. 16, Aug. 1992, Mark W. Holladay et al. "Synthesis and Biological Activity of CCK Heptapeptide Analogues . . . " pp. 2919–2928.

*Primary Examiner*—Jill Warden
*Assistant Examiner*—S. G. Marshall
*Attorney, Agent, or Firm*—McAulay Fisher Nissen Goldberg & Kiel

[57] ABSTRACT

Compounds of formula I,

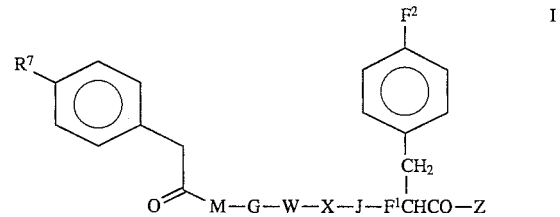

wherein M is Met, DMet, MeMet, MetO, Ahx, DAhx, MeAhx, Leu, MeLeu, Pro, Ile, MeIle, Ala or Lys, G is Gly, DAla, Pro, Ala, βAla or Sar; W is Trp, MeTrp, Ala or Nal; X is Met, MeMet, MetO, Ahx, MeAhx, Leu, MeLeu, Pro, Ile, MeIle, Ala, Phe, Lys or Lys($R^8$); J is Asp, DAsp, MeAsp, Asp(OBn), Ala or MeDAsp; $F^1$ is (S)—NH, (R)—NH, (S)—$R^1$N or (R)—$R^2$N; $F^2$ is H, Cl, I, Br, F, $NO_2$, $NH_2$, $R^3$ or $OR^4$; Z is $NH_2$, $NHR^5$ or $NR^5R^6$; $R^1$, $R^2$, $R^3$, $R^5$ and $R^6$ are alkyl $C_{1-6}$; $R^4$ is H or alkyl $C_{1-4}$; R is OH or $OSO_3H$; and pharmaceutically acceptable derivatives thereof; are useful as therapeutic agents, in particular in the inhibition of feeding.

1 Claim, No Drawings

PEPTIDE COMPOUNDS HAVING THERAPEUTIC ACTIVITY

This is a continuation of application Ser. No. 07/994,542, filed Dec. 21, 1992, now abandoned, which, in turn, is a continuation-in-part of application Ser. No. 07/810,985, filed Dec. 20, 1991, now abandoned, which, in turn, is a continuation-in-part of International U.S. patent application PCT/US90/06739, filed Nov. 16, 1990, which, in turn, is a continuation-in-part of application Ser. No. 07/441,275, filed Nov. 29, 1989, and abandoned.

This invention relates to peptide compounds having therapeutic activity (in particular feeding inhibition), their use as pharmaceutical and cosmetic therapeutic agents, and formulations comprising them.

BACKGROUND OF THE INVENTION

CCK-8 (a peptide having the structure Asp-Tyr(SO$_3$H)-Met-Gly-Trp-Met-Asp-Phe-NH$_2$) is known to have feeding inhibition properties [see for example J. E. Morley, Minireview: 'The ascent of cholecystokinin—from gut to brain', Life Sciences, Vol. 30 (6), pp. 479–493, 1982].

A number of synthetic peptides having feeding inhibition properties are known, for example those disclosed in European Patent Applications 226217 and 268297. The peptides of the present invention differ from these in having an optionally sulphated hydroxyphenylacetic acid group at the N-terminal.

DETAILED DESCRIPTION

According to the invention there is provided a compound of formula I,

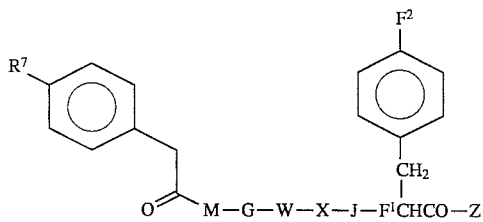

wherein

M is Met, DMet, MeMet, MetO, Ahx, DAhx, MeAhx, Leu, MeLeu, Pro, Ile, MeIle, Ala or Lys;

G is Gly, DAla, Pro, Ala, βAla or Sar;

W is Trp, MeTrp, Ala or Nal;

X is Met, MeMet, MetO, Ahx, MeAhx, Leu, MeLeu, Pro, Ile, MeIle, Ala, Phe, Lys or Lys(R$^8$);

J is Asp, DAsp, MeAsp, Asp(OBn), Ala or MeDAsp;

F$^1$ is (S)—NH, (R)—NH, (S)—R$^1$N or (R)—R$^2$N;

F$^2$ is H, Cl, I, Br, F, NO$_2$, NH$_2$, R$^3$ or OR$^4$;

Z is NH$_2$, NHR$^5$ or NR$^5$R$^6$;

R$^1$, R$^2$, R$^3$, R$^5$ and R$^6$ are alkyl C$_{1-6}$;

R$^4$ is H or alkyl C$_{1-6}$;

R$^7$ is OH or OSO$_3$H; and

R$^8$ is a group of formula II,

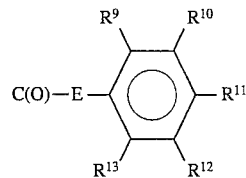

wherein E is NH, CH=CH or CH$_2$CH$_2$; and R$^9$, R$^{10}$, R$^{11}$, R$^{12}$ and R$^{13}$ are independently H, OH, halogen, alkyl C$_{1-6}$ or OSO$_3$H; or a pharmaceutically acceptable derivative thereof (hereinafter referred to en bloc as "the compounds of the invention").

All optically active amino acids have the L-configuration unless otherwise indicated. (R) and (S) indicate the absolute configuration about an adjacent methine carbon atom.

The compounds of the invention, amino acids, peptides and protecting groups are represented by symbols commonly used in the art, for example those defined by IUPAC and IUB. Examples of symbols are given below:

| | |
|---|---|
| Ahx | 2-aminohexanoic acid |
| Ala | alanine |
| Asn | asparagine |
| Asp | aspartic acid |
| Asp(OBn) | aspartic acid; β-benzyl ester |
| βAsp | β-aspartic acid |
| Asp(OtBu) | aspartic acid beta-tert-butyl ester |
| Boc | tert-butyloxycarbonyl |
| BrCH$_2$—Pam | 4-(bromomethyl)phenyl-acetamidomethyl |
| DAla | D-alanine |
| DAhx | D,2-aminohexanoic acid |
| DAsp | D-aspartic acid |
| DMet | D-methionine |
| DPhe | D-phenylalanine |
| DPhe—NH$_2$ | D-phenylalanine amide |
| DTrp | D-tryptophan |
| DTyr | D-tyrosine |
| EtPhe | N-ethylphenylalanine |
| EtPhe—NH$_2$ | N-ethylphenylalanine amide |
| Fmoc | 9-fluorenylmethyloxycarbonyl |
| Gly | glycine |
| HOBt | 1-hydroxybenzotriazolyl |
| Hpa | 4-hydroxyphenylacetic acid |
| Hpa(SO$_3$H) | O-sulpho-4-oxyphenylacetic acid |
| Ile | isoleucine |
| Leu | leucine |
| Lys | lysine |
| MeAhx | N-Methyl-2-aminohexanoic acid |
| MeAsp | N-methylaspartic acid |
| MeDAsp | N-methyl D-aspartic acid |
| MeLeu | N-methylleucine |
| MeIle | N-methylisoleucine |
| MeMet | N-methylmethionine |
| MePhe | N-methylphenylalanine |
| MePhe—NH$_2$ | N-methylphenylalanine amide |
| Met | methionine |
| MetO | methionine sulphoxide |
| MeTrp | N-α-methyltryptophan |
| MeTyr | N-methyltyrosine |
| Nle | norleucine (or 2-aminohexanoic acid) |
| OBt | 1-benzotriazolyl ester |
| OCH$_2$—Pam | 4-oxymethylphenylacetamidomethyl |
| OSu | succinimidyloxy ester |
| OtBu | tert-butylester |
| Phe | phenylalanine |
| Phe—NH$_2$ | phenylalanine amide |
| Phe—NHEt | phenylalanine ethylamide |
| Phe—NHMe | phenylalanine methylamide |
| Phe—N(Et)$_2$ | phenylalanine diethylamide |
| Phe—N(Me)$_2$ | phenylalanine dimethylamide |
| Phe—OH | phenylalanine acid |
| Phe(4-Cl) | 3-(4-chlorophenyl)alanine |
| Phe(4-Cl)—NH$_2$ | 3-(4-chlorophenyl)alanine amide |
| Phe(4-Me) | 3-(4-methylphenyl)alanine |
| Phe(4-Me)—NH$_2$ | 3-(4-methylphenyl)alanine amide |

3
-continued

| | |
|---|---|
| Phc(4-NO$_2$) | 3-(4-nitrophenyl)alanine |
| Phe(4-NO$_2$)—NH$_2$ | 3-(4-nitrophenyl)alanine amide |
| Phe(4-NH$_2$) | 3-(4-aminophenyl)alanine |
| Phe(4-NH$_2$)—NH$_2$ | 3-(4-aminophenyl)alanine amide |
| Pro | proline |
| resin | polystyrene |
| Sar | sarcosine |
| tBu | tert-butyl |
| Thr | threonine |
| Trp | tryptophan |
| Trp(Me) | 1-methyltryptophan |
| Tyr | tyrosine |
| Tyr—NH$_2$ | tyrosine amide |
| Tyr(Me) | O-methyltyrosine |
| Tyr(Me)—NH$_2$ | O-methyltyrosine amide |
| Tyr(SO$_3$H) | O-sulphotyrosine |

Thus, Hpa(SO$_3$H)-Met-Gly-Trp-Met-Asp-MePhe-NH$_2$ is the compound of formula I in which R$^7$ is OH, M is Met, G is Gly, W is Trp, X is Met, J is Asp, F$^1$ is (S)—CH$_3$N, F$^2$ is H and Z is NH$_2$:

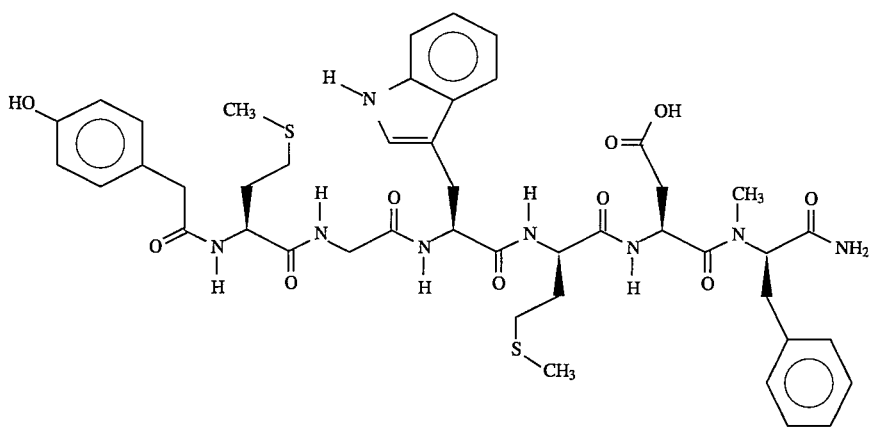

By Lys(R$^8$) we mean a lysine residue in which the ε-amino group forms an amide bond with a group of formula II, as defined above. Two particular groups of formula II which may be mentioned are the group in which E is NH, R$^9$ is methyl and R$^{10-13}$ are each hydrogen, ie (2-methylphenyl)aminocarbonyl, also referred to herein as "Tac"; and the group in which E is trans-CH=CH, R$^{11}$ is OH and R$^9$, R$^{10}$, R$^{12}$ and R$^{13}$ are each hydrogen.

Pharmaceutically acceptable derivatives of the compounds of formula I include esters and amides of any carboxylic acid groups which may be present, and pharmaceutically acceptable salts. Pharmaceutically acceptable derivatives which may be mentioned include unsubstituted amides of carboxylic acid groups (for example Asp may be present as its unsubstituted amide derivative Asn) and alkyl C$_{1-4}$ (for example methyl) esters of carboxylic acid groups. Pharmaceutically acceptable salts which may be mentioned include sodium and ammonium salts. Pharmaceutically acceptable derivatives of compounds of formula I may be prepared from the corresponding compound of formula I by conventional methods.

The term "pharmaceutically acceptable" used herein should be construed to mean that the compound, derivative, salt or other substance to which it refers is suitable for administration to the body as a pharmaceutical or cosmetic therapeutic agent. Similarly, terms such as "use as a pharmaceutical", "pharmaceutical formulation" and "method of treatment" include use as a cosmetic therapeutic agent, a cosmetic therapeutic formulation and a cosmetic method of treatment respectively.

Preferably M is Met, Ahx or Ile; G is Gly; W is Trp; X is Met, Ahx, Ile or Lys(R$^8$); J is Asp, DAsp, MeAsp or MeDAsp; F$^1$ is (S)—NH or (S)—R$^1$N; F$^2$ is H; and R$^7$ is OSO$_3$H.

According to a further aspect of the invention, there is provided a process for the preparation of a compound of formula I, or a pharmaceutically acceptable derivative thereof, which comprises:

a) sulphating a compound of formula III,

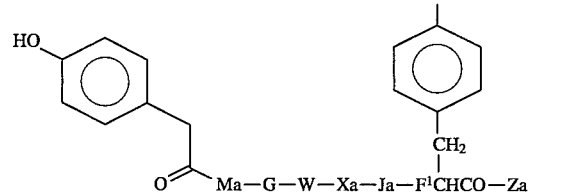

wherein G, W and F$^1$ are as defined in claim 1; Ma and Xa have the same definition as M and X in claim 1, except that the epsilon-amino group of any Lys residue present is protected; Ja has the same definition as J in claim 1, except that the beta carboxyl group of any Asp, DAsp, MeAsp or MeDAsp residue present is protected; F$^2$a has the same definition as F$^2$ in claim 1, except that any hydroxy or amino group is present in protected form; Za has the same definition as Z in claim 1, except that it may additionally represent a carboxyl protecting group;

b) removing one or more protecting groups from a compound of formula IV,

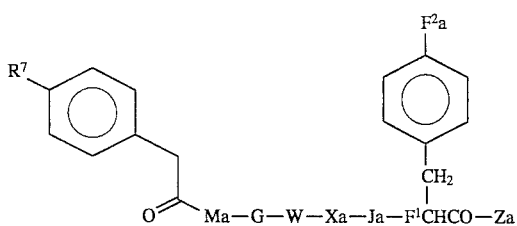

wherein $R^7$, G, W, and $F^1$ are as defined in claim 1; Ma, Xa, Ja, $F^2a$ and Za are as defined in process alternative (a); and at least one of Ma, Xa, Ja, $F^2a$ and Za comprises a protecting group;

c) reacting a compound of formula V,

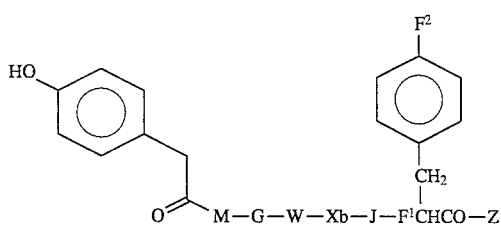

wherein M, G, W, J, Z, $F^1$ and $F^2$ are as defined in claim 1, and Xb is Lys, with a compound of formula VI,

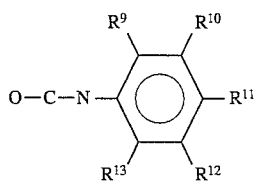

wherein $R^9$, $R^{10}$, $R^{11}$, $R^{12}$ and $R^{13}$ are as defined in claim 1, to give a corresponding compound of formula I in which X is Lys($R^8$) and E is NH; or d) coupling a compound of formula V as defined in process alternative (c) with a compound of formula VII,

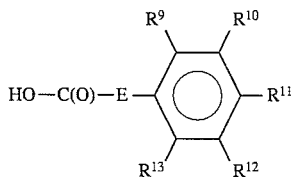

wherein E is $CH_2CH_2$ or CH=CH and $R^9$, $R^{10}$, $R^{11}$, $R^{12}$ and $R^{13}$ are as defined in claim 1, to give a corresponding compound of formula I in which X is Lys($R^8$) and E is $CH_2CH_2$ or CH=CH.

The invention provides intermediate compounds of formula IV per se.

In process (a), the sulphating agent may be, for example, sulphur trioxide or a complex thereof, such as sulphur trioxide pyridine. We particularly prefer to carry out the sulphation in a polar aprotic solvent, for example, dimethylformamide or pyridine. The reaction is preferably carried out using an excess of suplhating agent, for example a 1–40 molar excess, preferably a 5 molar excess.

In processes (a) and (b), protecting groups for peptides and methods for their removal are well known in the art, see for example, T. W. Green, Protective Groups in Organic Synthesis, Wiley-Interscience (1981). The choice of protecting groups and the methods employed for their removal will depend, inter alia, on the method of synthesis employed for the preparation of the peptide and the amino acids in the peptide. Suitable amino protecting groups include, for example, benzyloxycarbonyl, which may readily be removed by hydrogenolysis or hydrogen bromide in acetic acid; t-butyloxycarbonyl, (Boc), which is removed by standing the peptide in cold trifluoroacetic acid; Fmoc, which may be removed by treatment with dilute piperidine (20% in DMF); (4-methoxybenzyl)oxycarbonyl and 2-nitrophenylsulphenyl. The Boc and Fmoc groups are particularly preferred.

Suitable carboxyl protecting groups that Za may include are, for example, methyl, tert-butyl, benzyl and 4-methoxybenzyl. We particularly prefer benzyl, which may be readily removed by treatment with alcoholic amine or ammonia to give the corresponding amides. Similar groups may be used to protect the amino group in lysine and the carboxyl group in aspartic acid.

When the peptide is prepared using solid phase techniques, for example those in which the carboxyl end of the peptide is attached to a solid phase resin, linkage of the peptide to the resin acts as a carboxyl protecting group. Cleavage of the peptidyl-resin linkage will deprotect the carboxyl terminus of the peptide. Since the peptide end products of this invention are carboxyl terminal amides, the chemical link which connects the peptide chain to the resin must be such that its cleavage with suitable reagents readily provides amides. Due to the lability of the sulphate ester group to strong acids (for example, liquid hydrogen fluoride), the peptidyl-resin linkage may be cleavable with either weaker acids (for example, brief treatment with trifluoroacetic acid, TFA) and/or nucleophiles (for example, ammonia, amines, hydroxide, and alkoxides).

Process (c) may be carried out in an inert solvent, for example DMF, in the presence of a base such as N-methylmorpholine, and at a temperature of, for example, from 0°–50° C.

Process (d) may be carried out using an activated ester derivative of the acid. A suitable activated ester derivative is the N-hydroxy succinimidyl ester. The reaction may be carried out in the presence of a base such as N-methylmorpholine, under similar conditions to those described for process (c) above.

Among suitable resin derivatives may be mentioned oxymethyl-polystyrene, 4-(oxymethylphenyl)-$(CH_2)_a$-aminomethyl-polystyrene (n=0–3) and 4-(oxymethylphenyl)-oxymethyl-polystyrene. Similarly substituted polyacrylamide resins are equally well suited as the above polystyrene based resins. The term "polystyrene" includes copolymers with minor amounts, usually 1%, of unsaturated monomers such as divinylbenzene.

4-(Oxymethylphenyl)-$CH_2CO$-aminomethyl-polystyrene [herein referred to as 4-(oxymethylphenyl)-acetamidomethylpolystyrene or $OCH_2$-Pam-resin] is particularly preferred for the generation of peptide amides. This linkage may readily be cleaved to give the peptides of formula I by reaction with methanolic solutions of ammonia, alkylamines or dialkylamines as required.

Another resin which may be mentioned is a polystyrene resin (P) in which the backbone linkage to the peptide is,

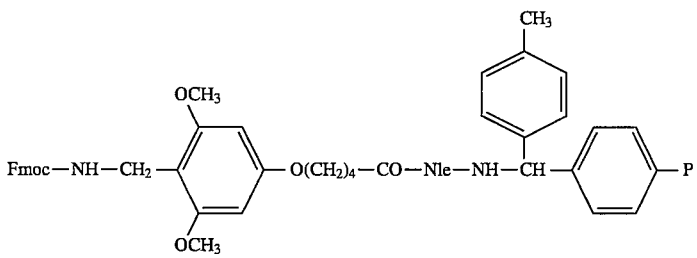

and herein referred to as [[5-[(4-Fmoc-aminomethyl)-3,5-dimethoxyphenoxy]valeroyl]norleucyl] -4'-methylbenzhydrylamine divinylbenzene polystyrene or PAL resin. PAL resin is particularly preferred for the generation of peptide amides in which X is not Lys. The linkage between the assembled peptide and this resin may be cleaved readily by reaction with the reagent formed by mixing TFA (trifluoroacetic acid), phenol, thioanisole, water and ethanedithiol in the proportions 8.5:0.5:0.5:0.5:0.2.

Another resin which may be substituted for the PAL resin is a polystyrene resin (P) in which the backbone linkage to the peptide is

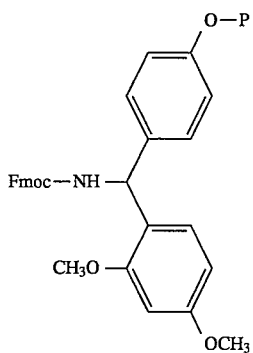

and referred to as 4-[(2,4-dimethoxyphenyl)(Fmoc-amino)methyl]phenoxydivinylbenzene polystyrene or Rink resin. The linkage may be readily cleaved in the same manner as for PAL resin.

The peptides of formulae III, IV and V may be prepared by methods well known to those skilled in the art. For example, they may be prepared by combining individual amino acids on a solid phase resin on a step-by-step basis, or alternatively, by combining groups of amino acids on a solid phase resin to yield the desired peptidyl-resin intermediate. Such additions are accomplished by protecting the amino group of the amino acid or group of amino acids by converting it to, for example, its tert-butyloxycarbonyl(Boc) or 9-fluorenylmethyl-oxycarbonyl (Fmoc) derivative, and then activating the carboxylic group of such amino acid or group of amino acids by converting it, for example, to its 1-hydroxybenzotriazole (HOBt) or N-hydroxysuccinimide (HOSu) ester derivative. Such a protected-activated intermediate is then allowed to react with an amino acid resin or peptidyl-resin with a free amino group, thus extending the peptide chain to provide the desired peptidyl-resin.

The C-terminal amino acid of the peptide to be prepared may be attached to the OCH$_2$-Pam-resin in several ways. For example, Boc-protected N-methylphenylalanine, may be reacted with a suitable 4-(bromomethyl)-phenylacetate ester (for example, phenacyl ester) and processed further to provide Boc-MePhe-(4-oxymethylphenyl)acetic acid which may be coupled to aminomethyl-polystyrene to provide Boc-MePhe-(4-oxymethylphenyl)acetamidomethylpolystyrene (Boc-MePhe-OCH$_2$-Pam-resin). Alternatively, 4-(bromomethyl)phenylacetic acid may be coupled to aminomethylpolystyrene to provide 4-(bromomethyl)phenylacetamidomethylpolystyrene (BrCH$_2$-Pam-resin) which may be reacted with the caesium salt of Boc-MePhe-OH to provide Boc-Phe-OCH$_2$-Pam-resin.

The C-terminal amino acid may be attached to the PAL resin by removal of the Fmoc protecting group with base, for example, piperidine, in a suitable solvent or mixture of solvents, for example, DMF and toluene, and then coupling the protected activated amino acid in the normal manner for solid phase synthesis. A particularly preferred method of activating the carboxyl group is to form the N-hydroxybenzotriazole (HOBt) ester in the presence of diisopropylcarbodiimide (DIPCDI). Suitable solvent systems, for example, dimethylformamide (DMF) and dichloromethane (DCM) may be used for this preactivation procedure.

Among the suitable activating groups may be mentioned any combination of groups which causes the acid function of the amino acid to become more reactive, such as acid chlorides, mixed and symmetrical anhydrides, reaction product with carbodiimide (for example, dicyclohexylcarbodiimide, DCC), and active esters (for example, esters derived from HOBt, HOSu, 2- or 4-nitrophenol, and 2,4,5-trichlorophenol). The use of DCC and esters of HOBt and HOSu is particularly preferred from the standpoint of yield, lack of by-products, and consequent ease of purification.

An automatic peptide synthesizer may be used for the solid phase synthesis of the sulphated peptide amides of this invention. The sulphate ester containing peptides of formula I may be desalted and purified by the usual methods. For example, the product may be purified by ion-exchange chromatography with the use of Trisacryl M DEAE, DEAE-cellulose or the like, partition chromatography with the use of Sephadex LH-20, Sephadex G-25 or the like, reverse phase chromatography with the use of Amberlite XAD-2 (or Biorad SM-2), ODS-silica gel or the like, normal phase chromatography with the use of silica gel or the like, or high-performance liquid chromatography (HPLC).

The protocol of coupling onto an aminomethyl-resin or peptidyl-OCH$_2$-Pam-resin (1 mmole of available nitrogen), deprotection, sulphation, cleavage, and product purification is set forth in Table 1.

TABLE 1

Protocol for Solid Phase Synthesis of Sulphated Peptid Amides on Pam-resin (1 mmole scale)

| Step | Reagent or Solvent | Purpose | Mix Time |
|---|---|---|---|
| 1 | DCM | Wash | 1 min |
| 2 | Go to step 3, 5 or 8 | — | — |
| 3 | Add filtered, pre-activated (0° C., 1 hr) | Pre-activated | 2–15 hr |

TABLE 1-continued

Protocol for Solid Phase Synthesis of Sulphated Peptid Amides on Pam-resin (1 mmole scale)

| Step | Reagent or Solvent | Purpose | Mix Time |
|---|---|---|---|
| | mixture of protected amino acid (or protected dipeptide, 3 mmole), HOBt (4.5 mmole), and DCC (3 mmole) in 1:4 DMF/DOC | DCC/HOBt coupling | |
| 4 | Go to step 10, 16, 21 or 26 | — | — |
| 5 | Add protected amino acid (or protected dipeptide, 3 mmole) in and HOBt (4.5 mmole) in 30 ml 1:2 DMF/DCM then DCC (3 mmole) in 20 ml DCM | In situ activated DCC/HOBt coupling | 2–15 hr |
| 6 | 2-propanol | Wash | 1 min |
| 7 | Go to step 10, 16, 21 or 26 | — | — |
| 8 | Add active ester or anhydride (3 mmole) in DCM, DMF or a mixture thereof | Non DCC/HOBt activated coupling | 2–15 hr |
| 9 | Go to step 10, 16, 21 or 26 | — | — |
| 10 | DCM | Wash | 1 min |
| 11 | Treat with 49:1 TFA/anisole/DCM | Boc and tBu removal | 30 min |
| 12 | DCM | Wash | 1 min |
| 13 | Treat with 1:19 DIEA*/DCM | Neutralise | 1 min |
| 14 | DCM | Wash | 1 min |
| 15 | Go to step 10, 16, 21 or 26 | — | — |
| 16 | DMF | Wash | 1 min |
| 17 | Treat with 1:4 piperidine/DMF | Fmoc removal | 3 min |
| 18 | Treat with 1:4 piperidine/DMF | Fmoc removal | 7 min |
| 19 | DMF | Wash | 1 min |
| 20 | Go to step 10, 16, 21 or 26 | — | — |
| 21 | DMF | Wash | 1 min |
| 22 | 1:2 pyridine/DMF | Wash | 1 min |
| 23 | Add sulphur trioxide pyridine complex (40 mmole) in 60 ml 1:2 pyridine/DMF | Sulphation | 20–24 hr |
| 24 | DMF | Wash | 1 min |
| 25 | Go to step 10, 16, 21 or 26 | — | — |
| 26 | Methanol | Wash | 1 min. |
| 27 | Ammonia saturated (−20° C.) methanol or 20% methanolic amine (250 ml) | Resin cleavage | 2–5 days |
| 28 | Methanol | Wash | 1 min |
| 29 | Combine and concentrate filtrates from steps 27–28 | Isolation | — |
| 30 | Chromatograph residue on column(s) of Amberlite XAD-2 (Rohm and Haas, 2.5 × 60 cm, methanol gradient 0.1 M in ammonia), Trisacryl M DEAE (LKB Inc, 2.5 × 47 cm, ammonium bicarbonate gradient), and/or P-40 ODS-3 (Whatman, 4.8 × 50 cm, methanol gradient 0.2% in ammonium acetate). | Purification | — |

*DIEA is diisopropylethylamine

A general procedure for the synthesis of non-sulphated peptide amides on PAL-resin (1 g scale) is set out in Table 2.

TABLE 2

| Step | Reagant or Solvent | Purpose | Mix Time |
|---|---|---|---|
| 1 | DCM | wash | 1 min |
| 2 | DCM/DMF (1:1) | wash | 1 min |
| 3 | 30% Piperidine 35% DMF 35% Toluene | Fmoc removal | 3 min |
| 4 | Repeat 3 | Fmoc removal | 7 min |
| 5 | DCM/DMF (1:1) | wash (10×) | 25 sec |
| 6 | Go to step 7 or 11 | — | — |
| 7 | Preactivated-protected amino acid [room temperature, Fmoc-aa-OH, DIPCDI (1 eq), HOBt (1 eq), in DMF:DCM(1:4)] | Pre-activation [Omit HOBt if preceding amino acid is MeAsp—, MeDAsp or MePhe—] | 10 min |
| 8 | Add to resin or resin-peptide | Coupling | 1–2 hr. |
| 9 | DCM/DMF (1:1) | Wash (4×) | 1 min |
| 10 | Go to step 3 [Repeat sequence 3–10 as necessary to complete peptide sequence] | — | — |
| 11 | Preactivated Hpa—Osu [Hpa—OH (1 eq), HO—Su (1 eq); DMF] | Pre-activation | 10 min |
| 12 | Add to resin-peptide | Coupling | 1–2 hr |
| 13 | DCM | Wash (4×) | 1 min |
| 14 | MeOH | Wash (4×) | 1 min |
| 15 | TFA/phenol/thioanisole/water/ethanedithiol [8.5:0.5:0.5:0.5:0.2] | Cleavage from resin | 2–3 hr. |
| 16 | TFA | Filter resin and wash | — |
| 17 | Combine and concentrate filtrates from step 16 | Isolation of peptide | — |
| 18 | Chromatograph residue on column(s) of Amberlite XAD-2 (Biorad SM-2 200–400 mesh, MeOH gradient 0.1 M in ammonia) and/or C-18 (ODS-3 Amicon, MeOH gradient, 0.1% in triethylamine, 0.1% In glacial acetic acid) and/or Amberlite XAD-2 (MeOH gradient). | Purification | — |
| 19 | Combine and concentrate purified fractions by freeze drying from 0–1 M NH$_3$ | Isolation | |

Modifications of the protocols in Tables 1 and 2 which may be applicable may readily be determined by experimentation.

Analogous procedures, wherein the reactions are carried out without the solid phase component (resin), are well known in the art and are well suited to large scale production (see for example U.S. Pat. No. 3,892,726).

The compounds of the invention bind to cholecystokinin receptors. Distinct CCK receptors in peripheral and brain tissues have been classified as CCK-A and CCK-B receptors respectively. Differentiation between agonist and antagonist interactions at CCK receptors can also be determined by functional assays. Activation of CCK-A receptors in peripheral tissues plays an important role in the control of pancreatic secretion, gut motility and gall bladder contraction. Thus compounds with agonist activity at CCK-A receptors have utility in the treatment of obesity and motility disorders and compounds with antagonist activity at CCK-A receptors may have utility in gastrointestinal disorders such as irritable bowel syndrome, ulcers, excess pancreatic or gastric secretion, acute pancreatitis and motility disorders. Therefore, compounds intended for use as therapeutic agents in the inhibition of feeding are likely to lack unwanted side-effects if they bind selectively to CCK-A receptors (rather than CCK-B receptors).

Pharmacological activity of the compounds of the invention can be demonstrated in Tests A–D below.

TEST A

Feeding Inhibition

Male Sprague-Dawley rats (weighing 300–350 g) are individually caged and maintained on a 12 hour light/dark cycle and trained for at least 14 days to feed during a three hour period of the dark cycle but not the 21 hours preceding that three hour period. On the day of the study, rats are dosed intraperitoneally with saline (controls) or test compound (dissolved in saline; usually a t a concentration of 0.3 to 300 µg of test compound per kg of rat weight). Food is introduced 10 minutes after administration of saline or test compound. A test compound is deemed to be active if the test group consumes significantly less food than the saline controls during the feeding period, which ends either 0.5 or three hours after presentation of the food.

TEST B

CCK-A Binding

Evaluation of a test compound for its ability to bind to CCK-A receptors in rat pancreatic membranes is measured against the binding of Bolton Hunter$^{125}$I-CCK-8 and $^{3}$H-L364718 to rat pancreas according to the procedures of Chang, Lotti, Chan and Kunkel (Molecular Pharmacology, 30:212–216, 1986).

TEST C

CCK-B Binding

Evaluation of a test compound for its ability to bind to CCK-B receptors in rat cerebral cortex membranes is measured against $^{125}$I-CCK-8 according to the procedures of Chang and Lotti (Proc, Natl. Acad. Sci. Vol. 83, 4923–4926).

TEST D

Functional Assay for CCK-A Agonist/Antagonist Activity

The evaluation of a test compound for its ability to inhibit or stimulate amylase release by rat pancreatic tissue fragments (acinar cells) is measured according to the procedures of Lin et al (J Pharm & Exper Therapeutics, 1986, 729–734) and Jung (Clinica Chema Acta, 1980, 100, 7–11).

Therefore, the invention also provides the use of a compound of the invention as a pharmaceutical.

According to a further aspect of the invention there is provided the use of a compound of the invention in the manufacture of a medicament for the treatment of obesity.

According to the invention there is also provided a method of treatment of obesity which comprises administering a therapeutically effective amount of a compound of the invention to a patient in need of such treatment.

According to a further aspect of the invention there is also provided a pharmaceutical formulation comprising (preferably less than 80%, and more preferably less than 50% by weight of) a compound of the invention in combination with a pharmaceutically acceptable adjuvant, diluent or carrier.

The compounds of the invention may be administered by a variety of routes, for example, orally, intraperitoneally, intravenously, intramuscularly, subcutaneously or intranasally. The dosage of the compounds of the invention will depend on several factors, including the requirements of the recipient, but will typically be in the range 0.3 µg to 3.0 mg per kg of body weight per day, either in a single dose or divided among two to four doses.

Examples of suitable adjuvants, diluents or carriers are:

for tablets and dragees, lactose, starch, talc or stearic acid;

for capsules; tartaric acid or lactose;

for injectable solutions; water, alcohols, glycerin or vegetable oils.

The compositions may also contain suitable preserving, stabilising and wetting agents, solubilisers (eg a water-soluble cellulose polymer such as hydroxypropyl methylcellulose, or a water-soluble glycol such as propylene glycol), sweetening and colouring agents and flavourings. The compositions may, if desired, be formulated in sustained release form.

The compounds of the invention have the advantage that they are more efficacious, more potent, longer acting, more stable (particularly to enzymatic degradation), more selective, less toxic, give rise to fewer side effects, are more readily absorbed, are quicker acting, or have other advantageous pharmacological effects, in comparison with the compounds of the prior art.

The invention is illustrated by the following examples, in which an automatic peptide synthesizer was used for solid phase synthesis.

EXAMPLE 1

Boc-MePhe(4-oxymethylphenyl)acetic Acid

To a solution of Boc-MePhe-OH (27.93 g) and 4-(bromomethyl)phenylacetic acid phenacyl ester (33.32 g) in acetonitrile (1 l) was added potassium fluoride dihydrate (18.28 g). The suspension was stirred overnight, filtered and the filtrate evaporated to dryness. The residue, Boc-MePhe-(4-oxymethylphenyl)acetic acid phenacyl ester, was dissolved in 85% acetic acid (1.2 l), treated with zinc dust (128 g), and stirred for 2–4 hours. Concentration of the filtered reaction mixture to about 400 ml and dilution with 3.2 ml of water gave an oil which was dissolved in ethyl acetate and treated with dicyclohexylamine (DCHA) to give 41.31 g of the DCHA salt of the title compound, mp 120°–122° C.

The following compounds were prepared using essentially the same procedures:

Boc-EtPhe-(4-oxymethylphenyl)acetic acid, mp 137°–141° C. (DCHA salt);

Boc-Phe(4-Cl)-(4-oxymethylphenyl)acetic acid;

Boc-Tyr(Me)-(4-oxymethylphenyl)acetic acid, mp 64°–67° C. (free base);

Fmoc-Tyr(tBu)-4-(oxymethylphenyl)acetic acid, 192°–195° C. (free base).

EXAMPLE 2

H-MePhe-OCH$_2$-Pam-resin

Boc-MePhe-(4-oxymethylphenyl)acetic acid (the product of Example 1, 1.82 g, 3 mmole of its DCIIA salt) and HOBt (6.9 g, 4.5 mmole) in 40 ml of 1:3 DMF/DCM (dimethylformamide/dichloromethane) followed by DCC (1,3-dicyclohexylcarbodiimide, 0.62 g, 3 mmole) in 20 ml of DCM were added to aminomethylpolystyrene resin (1.34 g, 1 mmole available nitrogen) to give a suspension which was shaken for 2 to 15 hours. Boc-MePhe-OCH$_2$-Pam-resin was isolated by filtration, washed with 2-propanol and DCM, and treated according to Table 1 (steps 10–14) to give the title compound as the free base.

H-EtPhe-OCH$_2$-Pam-resin was prepared using essentially the same procedure.

EXAMPLE 3

H-Phe-OCH$_2$-Pam-resin

Boc-Phe-(4-oxymethylphenyl)acetic acid (prepared by the method of Example 1, 0.83 g, 2 mmole), 1-hydroxybenzotriazole (HOBt, 0.46 g, 3 mmole) and DCC (0.41 g, 2 mmole) were dissolved in 50 ml of 4:1 DCM/DMF and stirred at 0° C. for 1 hour. Aminomethylpolystyrene resin (1.34 g, 1 mmole available nitrogen) was suspended in the filtered reaction mixture (precipitated DCU removed) and shaken for 2–15 hours. The product, Boc-Phe-OCH$_2$-Pam-resin, was isolated by filtration and treated according to Table 1 (steps 10–14) to give the title compound.

H-Phe(4-Cl)-OCH$_2$-Pam resin and H-Tyr(Me)-OCH$_2$-Pam-resin were prepared using essentially similar procedures.

EXAMPLE 4

Fmoc-Met-Asp(OtBu)-OH

Fmoc-Met-OSu was prepared in situ by the reaction of Fmoc-Met-OH (14.87 g), HOSu (5.52 g) and DCC (8.26 g) in THF (tetrahydrofuran, 200 ml) at 0° C. for 3.5 hours. Precipitated dicyclohexylurea (DCU) was removed by filtration and the THF filtrate was added to a cold solution of H-Asp(OtBu)-OH in 220 ml of 10:1 water/THF to which had been added 40 ml of 1N sodium hydroxide. After stirring the reaction mixture at room temperature overnight, solid citric acid (20 g) was added along with ethyl acetate (600 ml). The ethyl acetate layer was separated, washed with 10% citric acid and brine, then dried (MgSO$_4$). Evaporation of the ethyl acetate solution gave a residue which was dissolved in ethyl acetate (200 ml) and treated with DCHA (7.84 ml) to precipitate 17.93 g of the DCHA salt of the title compound, mp 159°–162° C.

EXAMPLE 5

H-Phe(4-NO$_2$)-OCH$_2$-Pam-resin

Boc-Phe(4-NO$_2$)-OH (1.39 g) was dissolved in 70% methanol (100 ml) and adjusted to pH7 with the addition of 1N caesium bicarbonate. The solution was evaporated to dryness with the residue being evaporated three more times with added DMF. The resultant dried caesium salt of Boc-Phe(NO$_2$)-OH was dissolved in DMF (60 ml) and shaken with BrCH$_2$-Pam-resin (1 meq of Br) overnight. Boc-Phe(4-NO$_2$—OCH$_2$-Pam-resin was isolated by filtration, washed with DCM and treated according to Table 1 (steps 10–14) to give the title compound as a free base.

EXAMPLE 6

H-Tyr(tBu)—OCH$_2$-Pam-resin

Fmoc-Tyr(tBu)-(4-oxymethylphenyl)acetic acid (1.82 g, 3 mmole), 1-hydroxybenzotriazole (0.69 g, 4.5 mmole) and DCC (0.62 g, 3 mmole) were dissolved in 50 ml of 4:1 DCM/DMF and stirred at 0° C. for 1 hour. Aminomethyl-resin (1.34 g, 1 mmole available nitrogen) was suspended in the filtered reaction mixture (precipitated DCU removed) and shaken for 2–15 hours. Fmoc-Tyr(tBu)-OCH$_2$-Pam-resin was isolated by filtration and treated according to table 1 (steps 16–20) to give the title compound as a free base.

H-MeTyr(Me)-OCH$_2$-Pam-resin was prepared using essentially the same procedure.

EXAMPLE 7

Hpa(SO$_3$H)-Met-Gly-Trp-Met-Asp-Phe-NH$_2$ (SEQ ID NO 1)

H-Phe-OCH$_2$-Pam-resin (from example 3) was sequentially coupled with Fmoc-Asp(OtBu)-OH, Fmoc-Met-OH, Fmoc-Trp-OH, Fmoc-Gly-OH and Fmoc-Met-OH according to table 1 (coupling steps 5–7, followed by Fmoc removal steps 16–20) to provide H-Met-Gly-Trp-Met-Asp(OtBu)-Phe-OCH$_2$-resin which was coupled with 4-hydroxyphenylacetic acid N-hydroxysuccinimide ester (Hpa-OSu) according to table 1 (steps 10–15, steps 21–25 and then steps 26–29 with ammonia) to give the title compound which was chromatographically purified on Amberlite XAD-2, Trisacryl M DEAE and P40 ODS-3, sequentially, according to Table 1 (step 30) to give 100 mg of the ammonium salt of the title compound. Amino acid analysis following acid decomposition gave Asp 1.03 (1), Met 1.98 (2), Gly 1.02 (1) and Phe 0.98 (1). Infrared absorption spectrum showed a strong peak typical of a sulphuric acid ester at 1050 cm$^{-1}$.

EXAMPLE 8

Hpa(SO$_3$H)-Ala-Gly-Trp-Met-Asp-Phe-NH$_2$ (SEQ ID NO 2)

H-Phe-OCH$_2$-Pam-resin (the product of Example 3) was sequentially coupled with Fmoc-Asp(OtBu)-OH, Fmoc-Met-OH, Fmoc-Trp-OH, Fmoc-Gly-OH and Fmoc-Ala-OH according to table 1 (coupling steps 5–7 followed by Fmoc removal steps 16–20) to provide H-Ala-Gly-Trp-Met-Asp(OtBu)-Phe-OCH$_2$-Pam-resin which was coupled with Hpa-OSu according to table 1 (steps 8–9) to give Hpa-Ala-Gly-Trp-Met-Asp(OtBu)-Phe-OCH$_2$-Pam-resin which was deprotected, sulphated and cleaved from the resin according to table 1 (steps 10–15, steps 21–25 and then steps 26–29 with ammonia) to give the title compound which was chromatographically purified on Amberlite XAD-2 and P-40 ODS-3 sequentially, according to table 1 (step 30) to give 150 mg of the ammonium salt of the title compound. Amino acid analysis following acid decomposition gave Asp 1.18 (1), Met 0.85 (1), Ala 0.94 (1), Gly 1.09 (1) and Phe 0.92 (1).

Infrared absorption spectrum showed a strong peak typical of a sulphuric acid ester at 1050 cm$^{-4}$.

EXAMPLE 9

Hpa(SO₃H)-Met-Gly-Trp-Met-Asp-MePhe-NH₂
(SEQ ID NO 3)

H-MePhe-OCH$_2$-Pam-resin (the product of Example 2) was sequentially coupled with Fmoc-Met-Asp(OtBu)-OH, Fmoc-Trp-OH, Fmoc-Gly-OH and Fmoc-Met-OH according to table 1 (coupling steps 5–7 followed by Fmoc removal steps 16–20) to provide H-Met-Gly-Trp-Met-Asp(OtBu)-MePhe-OCH$_2$-Pam-resin which was coupled with Hpa-OSu according to table 1 (coupling steps 8–9) to give Hpa-Met-Gly-Trp-Met-Asp(OtBu)-MePhe-OCH$_2$-Pam-resin which was deprotected, sulphated and cleaved from the resin according to table 1 (steps 10–15, steps 21–25 and then steps 26–29 with ammonia) to give the title compound which was chromatographically purified on Amberlite XAD-2 and P-40 ODS-3, sequentially, according to table 1 (step 30) to give 130 mg of the ammonium salt of the title compound. Amino acid analysis following acid decomposition gave Met 1.95 (2), Asp 1.00 (1), Gly 0.97 (1) and MePhe 1.08 (1).

Infrared absorption spectrum showed a strong peak typical of a sulphuric acid ester at 1050 cm$^{-4}$.

EXAMPLE 10

Hpa(SO₃H)-Ala-Gly-Trp-Met-Asp-MePhe-NH₂
(SEQ ID NO 4)

H-MePhe-OCH$_2$-Pam-resin (the product of Example 2) was sequentially coupled with Fmoc-Met-Asp(OtBu)-OH, Fmoc-Trp-OH, Fmoc-Gly-OH and Fmoc-Ala-OH according to table 1 (coupling steps 5–7 followed by Fmoc removal steps 16–20) to provide H-Ala-Gly-Trp-Met-Asp(OtBu)-MePhe-OCH$_2$-Pam-resin which was coupled with Hpa-OSu according to table 1 (coupling steps 8–9) to give Hpa-Ala-Gly-Trp-Met-Asp(OtBu)-MePhe-OCH$_2$-Pam-resin which was deprotected, sulphated and cleaved from the resin according to table 1 (steps 10–15, steps 21–25 and then steps 26–29 with ammonia) to give the title compound which was chromatographically purified on Amberlite XAD-2 and P-40 ODS-3, sequentially, according to Table 1 (step 30) to give 180 mg of the ammonium salt of the title compound. Amino acid analysis following acid decomposition gave Ala 0.97 (1), Met 0.82 (1), Gly 1.00 (1), Asp 1.10 (1) and MePhe 1.11 (1).

Infrared absorption spectrum showed a strong peak typical of a sulphuric acid ester at 1050 cm$^{-1}$.

EXAMPLE 11

Hpa(SO₃H)-Met-DAla-Trp-Met-Asp-MePhe-NH₂

H-MePhe-OCH$_2$-Pam-resin was sequentially coupled with Fmoc-Met-Asp(OtBu)-OH, Fmoc-Trp-OH, Fmoc-DAla-OH and Fmoc-Met-OH according to table 1 (coupling steps 5–7 followed by Fmoc removal steps 16–20) to provide H-Met-DAla-Trp-Met-Asp(OtBu)-MePhe-OCH$_2$-Pam-resin which was coupled with Hpa-OSu according to table 1 (coupling steps 8–9) to give Hpa-Met-DAla-Trp-Met-Asp(OtBu)-MePhe-OCH$_2$-Pam-resin which was deprotected, sulphated and cleaved from the resin according to table 1 (steps 10–15, steps 21–25 and then steps 26–29 with ammonia) to give the title compound which was chromatographically purified on Amberlite XAD-2 and P-40 ODS-3, sequentially, according to table 1 (step 30) to give 40 mg of the ammonium salt of the title compound. Amino acid analysis following acid decomposition gave Asp 1.10 (1), Met 1.79 (2), Ala 0.98 (1) and MePhe 1.13 (1). Infrared absorption spectrum showed a strong peak typical of a sulphuric acid ester at 1050 cm$^{-1}$.

EXAMPLE 12

Hpa(SO₃H)-Met-Gly-Ala-Met-Asp-MePhe-NH₂
(SEQ ID NO 5)

H-MePhe-OCH$_2$-Pam-resin was sequentially coupled with Fmoc-Met-Asp(OtBu)-OH, Fmoc-Ala-OH, Fmoc-Gly-OH and Fmoc-Met-OH according to table 1 (coupling steps 5–7 followed by Fmoc removal steps 16–20) to provide H-Met-Gly-Ala-Met-Asp(OtBu)-MePhe-OCH$_2$-Pam-resin which was coupled with Hpa-OSu according to table 1 (coupling steps 8–9) to give Hpa-Met-Gly-Ala-Met-Asp(OtBu)-MePhe-OCH$_2$-Pam-resin which was deprotected, sulphated and cleaved from the resin according to table 1 steps 10–15, steps 21–25 and then steps 26–29 with ammonia) to give the title compound which was chromatographically purified on Amberlite XAD-2 and P-40 ODS-3, sequentially, according to table 1 (step 30) to give 30 mg of the ammonium salt of the title compound Amino acid analysis following acid decomposition gave Met 1.76 (2), Asp 1.12 (1), Gly 1.07 (1) Ala 1.03 (1) and MePhe 1.02 (1).

Infrared absorption spectrum showed a strong peak typical of a sulphuric acid ester at 1050 cm$^{-1}$.

EXAMPLE 13

Hpa(SO₃H)-Met-Gly-Trp-Ala-Asp-MePhe-NH₂
(SEQ ID NO 6)

H-MePhe-OCH$_2$-Pam-resin was sequentially coupled with Fmoc-Ala-Asp(OtBu)-OH, Fmoc-Trp-OH, Fmoc-Gly-OH and Fmoc-Met-OH according to table 1 (coupling steps 5–7 followed by Fmoc removal steps 16–20) to provide H-Met-Gly-Trp-Ala-Asp(OtBu)-MePhe-OCH$_2$-Pam-resin which was coupled with Hpa-OSu according to table 1 (coupling steps 8–9) to give Hpa-Met-Gly-Trp-Ala-Asp(OtBu)-MePhe-OCH$_2$-Pam-resin which was deprotected, sulphated and cleaved from the resin according to table 1 (steps 10–15, steps 21–25 and then steps 26–29 with ammonia) to give the title compound which was chromatographically purified on Amberlite XAD-2 and P-40 ODS-3, sequentially, according to table 1 (step 30) to give 140 mg of the ammonium salt of the title compound. Amino acid analysis following acid decomposition gave Ala 0.97 (1), Met 0.83 (1), Gly 0.97 (1), Asp 1.09 (1) and MePhe 1.15 (1).

Infrared absorption spectrum showed a strong peak typical of a sulphuric acid ester at 1050 cm$^{-1}$.

EXAMPLE 14

Hpa(SO₃H)-Met-Gly-Trp-Met-Ala-MePhe-NH₂
(SEQ ID NO 7)

H-MePhe-OCH$_2$-Pam-resin was sequentially coupled with Fmoc-Met-Ala-OH, Fmoc-Trp-OH, Fmoc-Gly-OH and Fmoc-Met-OH according to table 1 (coupling steps 5–7 followed by Fmoc removal steps 16–20) to provide H-Met-Gly-Trp-Met-Ala-MePhe-OCH$_2$-Pam-resin which was coupled with Hpa-OSu according to table 1 (coupling steps 8–9) to give Hpa-Met-Gly-Trp-Met-Ala-MePhe-OCH$_2$-Pam-resin which was deprotected, sulphated and cleaved from the resin according to table 1 (steps 10–15, steps 21–25 and then steps 26–29 with ammonia) to give the title compound which was chromatographically purified on Amberlite XAD-2 and P-40 ODS-3, sequentially, according to table 1 (step 30) to give 170 mg of the ammonium salt of the title compound. Amino acid analysis following acid decomposition gave Met 1.73 (2), Gly 0.98 (1), Ala 0.98 (1), and MePhe 1.31 (1).

Infrared absorption spectrum showed a strong peak typical of a sulphuric acid ester at 1050 cm$^{-1}$.

EXAMPLE 15

Hpa(SO$_3$H)-Ala-Gly-Trp-Ala-Asp-MePhe-NH$_2$
(SEQ ID NO 8)

H-MePhe-OCH$_2$-Pam-resin is sequentially coupled with Fmoc-Ala-Asp(OtBu)-OH, Fmoc-Trp-OH, Fmoc-Gly-OH and Fmoc-Ala-OH according to table 1 (coupling steps 5–7 followed by Fmoc removal steps 16–20) to provide H-Ala-Gly-Trp-Ala-Asp(OtBu)-MePhe-OCH$_2$-Pam-resin which is coupled with Hpa-OSu according to table 1 (coupling steps 8–9) to give Hpa-Ala-Gly-Trp-Ala-Asp(OtBu)-MePhe-OCH$_2$-Pam-resin which is deprotected, sulphated and cleaved from the resin according to table 1 (steps 10–15, steps 21–25 and then steps 26–29 with ammonia) to give the title compound which is chromatographically purified on Amberlite XAD-2 and P-40 ODS-3, sequentially, according to table 1 (step 30) to give the ammonium salt of the title compound.

EXAMPLE 16

Hpa(SO$_3$H)-Ahx-Gly-Trp-Ahx-Asp-MePhe-NH$_2$
(SEQ ID NO 9)

H-MePhe-OCH$_2$-Pam-resin was sequentially coupled with Fmoc-Ahx-Asp(OtBu)-OH, Fmoc-Trp-OH, Fmoc-Gly-OH and Fmoc-Ahx-OH according to table 1 (coupling steps 5–7 followed by Fmoc removal steps 16–20) to provide H-Ahx-Gly-Trp-Ahx-Asp(OtBu)-MePhe-OCH$_2$-Pam-resin, which was coupled with Hpa-OSu according to table 1 (coupling steps 8–9) to give Hpa-Ahx-Gly-Trp-Ahx-Asp(OtBu)-MePhe-OCH$_2$-Pam-resin which was deprotected, sulphated and cleaved from the resin according to table 1 (steps 10–15, steps 21–25 and then steps 26–29 with ammonia) to give the title compound, which was chromatographically purified on Amberlite XAD-2 and P-40 ODS-3, sequentially, according to table 1 (step 30) to give 80 mg of the ammonium salt of the title compound. Amino acid analysis following acid decomposition gave Ahx 1.93 (2), Asp 1.00 (1), Gly 0.97 (1) and MePhe 1.10 (1).

Infrared absorption spectrum showed a strong peak typical of a sulphuric acid ester at 1050 cm$^{-1}$.

EXAMPLE 17

Hpa(SO$_3$H)-Ile-Gly-Trp-Ile-Asp-MePhe-NH$_2$ (SEQ ID NO 10)

H-MePhe-OCH$_2$-Pam-resin was sequentially coupled with Fmoc-Ile-Asp(OtBu)-OH, Fmoc-Trp-OH, Fmoc-Gly-OH and Fmoc-Ile-OH according to table 1 (coupling steps 5–7 followed by Fmoc removal steps 16–20) to provide H-Ile-Gly-Trp-Ile-Asp(OtBu)-MePhe-OCH$_2$-Pam-resin which was coupled with Hpa-OSu according to table 1 (coupling steps 8–9) to give Hpa-Ile-Gly-Trp-Ile-Asp(OtBu)-MePhe-OCH$_2$-Pam-resin which was deprotected, sulphated and cleaved from the resin according to table 1 (steps 10–15, steps 21–25 and then steps 26–29 with ammonia) to give the title compound which was chromatographically purified on Amberlite XAD-2 and P-40 ODS-3, sequentially, according to table 1 (step 30) to give 50 mg of the ammonium salt of the title compound. Amino acid analysis following acid decomposition gave Ile 1.88 (2), Asp 1.02 (1), Gly 0.98 (1) and MePhe 1.12 (1).

Infrared absorption spectrum showed a strong peak typical of a sulphuric acid ester at 1050 cm$^{-1}$.

EXAMPLE 18

Hpa(SO$_3$H)-Ile-Gly-Trp-Ahx-Asp-MePhe-NH$_2$
(SEQ ID NO 11)

H-MePhe-OCH$_2$-Pam-resin was sequentially coupled with Fmoc-Ahx-Asp(OtBu)-OH, Fmoc-Trp-OH, Fmoc-Gly-OH and Fmoc-Ile-OH according to table 1 (coupling steps 5–7 followed by Fmoc removal steps 16–20) to provide H-Ile-Gly-Trp-Ahx-Asp(OtBu)-MePhe-OCH$_2$-Pam-resin which was coupled with Hpa-OSu according to table 1 (coupling steps 8–9) to give Hpa-Ile-Gly-Trp-Ahx-Asp(OtBu)-MePhe-OCH$_2$-Pam-resin which was deprotected, sulphated and cleaved from the resin according to table 1 (steps 10–15, steps 21–25 and then steps 26–29 with ammonia) to give the title compound which was chromatographically purified on Amberlite XAD-2 and P40 ODS-3, sequentially, according to table 1 (step 30) to give 120 mg of the ammonium salt of the title compound. Amino acid analysis following acid decomposition gave Ile 1.04 (1), Trp 0.82 (1), Asp 1.04 (1), Gly 1.03 (1) Ahx 1.03 (1) and MePhe 0.86 (1).

Infrared absorption spectrum showed a strong peak typical of a sulphuric acid ester at 1050 cm$^{-1}$.

EXAMPLE 19

Hpa(SO$_3$H)-Met-Ala-Trp-Met-Asp-MePhe-NH$_2$
(SEQ ID NO 12)

H-MePhe-OCH$_2$-Pam-resin was sequentially coupled with Fmoc-Met-Asp(OtBu)-OH, Fmoc-Trp-OH, Fmoc-Ala-OH and Fmoc-Met-OH according to table 1 (coupling steps 5–7 followed by Fmoc removal steps 16–20) to provide H-Met-Ala-Trp-Met-Asp(OtBu)-MePhe-OCH$_2$-Pam-resin which was coupled with Hpa-OSu according to table 1 (coupling steps 8–9) to give Hpa-Met-Ala-Trp-Met-Asp(OtBu)-MePhe-OCH$_2$-Pam-resin which was deprotected, sulphated and cleaved from the resin according to table 1 (steps 10–15, steps 21–25 and then steps 26–29 with ammonia) to give the title compound which was chromatographically purified on Amberlite XAD-2 and P-40 ODS-3, sequentially, according to table 1 (step 30) to give 60 mg of the ammonium salt of the title compound. Amino acid analysis following acid decomposition gave Met 1.89 (2), Asp 0.99 (1), Ala 0.99 (1) and MePhe 1.12 (1).

Infrared absorption spectrum showed a strong peak typical of a sulphuric acid ester at 1050 cm$^{-1}$.

EXAMPLE 20

Hpa(SO$_3$H)-Met-βAla-Trp-Met-Asp-MePhe-NH$_2$
(SEQ ID NO 13)

H-MePhe-OCH$_2$-Pam-resin was sequentially coupled with Fmoc-Met-Asp(OtBu)-OH, Fmoc-Trp-OH, Fmoc-βAla-OH and Fmoc-Met-OH according to table 1 (coupling steps 5–7 followed by Fmoc removal steps 16–20) to provide H-Met-βAla-Trp-Met-Asp(OtBu)-MePhe-OCH$_2$-Pam-resin which was coupled with Hpa-OSu according to table 1 (coupling steps 8–9) to give Hpa-Met-βAla-Trp-Met- Asp(OtBu)-MePhe-OCH$_2$-Pam-resin which was deprotected, sulphated and cleaved from the resin according to table 1 (steps 10–15, steps 21–25 and then steps 26–29 with ammonia) to give the title compound which was chromatographically purified on Amberlite XAD-2 and P-40 ODS-3, sequentially, according to table 1 (step 30) to give 41 mg of the ammonium salt of the title compound. Amino acid analysis following acid decomposition gave Met 1.94 (2), Asp 1.02 (1), βAla 0.84 (1) and MePhe 1.01 (1).

Infrared absorption spectrum showed a strong peak typical of a sulphuric acid ester at 1050 cm$^{-1}$.

EXAMPLE 21

Hpa(SO$_3$H)-Met-Gly-Trp-Met-DAsp-MePhe-NH$_2$

As a result of racemization during the synthesis of Example 9, Hpa(SO$_3$H)-Met-Gly-Trp-Met-DAsp-MePhe-NH$_2$ was isolated as a by-product during the purification of Example 9 according to Table 1 (Step 30) to give 47 mg of the ammonium salt of the title compound. Amino acid analysis following acid decomposition gave Met 1.80 (2), Gly 1.03 (1), Asp (1.06), and MePhe 1.11 (1). Infrared absorption spectrum showed a strong peak typical of a sulfuric acid ester at 1050 cm$_{-1}$. The presence of DAsp was verified by the method of Marfey (P. Marfey, Carlsberg Res Commun, 1984, 49, 591–596).

EXAMPLE 22

Hpa(SO$_3$H)-Ahx-Gly-Trp-Ahx-Asp-Phe-NH$_2$ (SEQ ID NO 14)

H-Phe-OCH$_2$-Pam-resin (the product of Example 3) was sequentially coupled with Fmoc-Asp(OtBu)-OH, Fmoc-Ahx-OH, Fmoc-Trp-OH, Fmoc-Gly-OH, Fmoc-Ahx-OH according to Table 1 (coupling steps 5–7 followed by Fmoc removal steps 16–20) to provide H-Ahx-Gly-Trp-Ahx-Asp(OtBu)-Phe-OCH$_2$-Pam-resin which was coupled with Hpa-OSu according to Table 1 (coupling steps 8–9) to give Hpa-Ahx-Gly-Trp-Ahx-Asp(OtBu)-Phe-OCH$_2$-Pam-resin which was deprotected, sulphated and cleaved from the resin according to Table 1 (steps 10–15, steps 21–25 and then steps 26–29 with ammonia) to give the title compound which was chromatographically purified on SM-2 and ODS-3 columns sequentially according to Table 2 (step 18). Amino acid analysis following acid decomposition gave Asp 1.03 (1), Gly 1.05 (1), Ahx 1.94 (2), Phe 0.99 (1), Trp 0.74 (1), NH$_3$ 2.16. MS (FAB): me/961 (M–H)$^-$.

EXAMPLE 23

Hpa-Met-Gly-Trp-Met-DAsp-Phe-NH$_2$

PAL-resin was deprotected and sequentially coupled according to Table 2 with Fmoc-Phe-OH, Fmoc-DAsp(OtBu)-OH, Fmoc-Met-OH, Fmoc-Trp-OH, Fmoc-Gly-OH, Fmoc-Met-OH and Hpa-OSu to provide the title compound. Amino acid analysis following acid decomposition gave Asp 1.05 (1), Gly 1.07 (1), Met 1.79 (2), Phe 1.10 (1), Trp 0.71 (1.0), NH$_3$ 1.40. MS (FAB): m/e 919 (M+H)$^+$.

EXAMPLE 24

Hpa-Ahx-Gly-Trp-Ahx-Asp-Phe-NH$_2$ (SEQ ID NO 15)

PAL-resin was deprotected and sequentially coupled according to Table 2 with Fmoc-Phe-OH, Fmoc-Asp(OtBu)-OH, Fmoc-Ahx-OH, Fmoc-Trp-OH, Fmoc-Trp-OH, Fmoc-Gly-OH, Fmoc-Ahx-OH and Hpa-OSu to provide the title compound. Amino acid analysis following acid decomposition gave Asp 1.00 (1), Gly 1.08 (1.0), Ahx 1.85 (2), Phe 1.10 (1), Trp 0.68 (1), NH$_3$ 1.00. MS (FAB): m/e 883 (M+H)$^+$.

EXAMPLE 25

Hpa-Ahx-Gly-Trp-Ahx-MeAsp-Phe-NH$_2$ (SEQ ID NO 16)

PAL-resin was deprotected and sequentially coupled according to Table 2 with Fmoc-Phe-OH, Fmoc-MeAsp(OtBu)-OH, Fmoc-Ahx-OH, Fmoc-Trp-OH, Fmoc-Gly-OH, Fmoc-Ahx-OH and Hpa-OSu, to give the title compound. Amino acid analysis following acid decomposition gave Gly 0.89 (1), MeAsp 1.04 (1), Ahx 1.99 (2), Phe 1.09 (1), Trp 0.71 (1), NH$_3$ 0.91. MS (FAB): m/e 897 (M+H)$^+$.

EXAMPLE 26

Hpa-Ile-Gly-Trp-Ile-DAsp-MePhe-NH$_2$

PAL-resin was deprotected and sequentially coupled according to Table 2 with Fmoc-MePhe-OH, Fmoc-DAsp(OtBu)-OH, Fmoc-Ile-OH, Fmoc-Trp-OH, Fmoc-Gly-OH, Fmoc-Ile-OH and Hpa-OSu, to give the title compound. Amino acid analysis following acid decomposition gave Asp 1.00 (1), Gly 1.14 (1), Ile 1.91 (2), MePhe 0.96 (1), Trp 0.64 (1), NH$_3$ 1.44. MS (FAB): m/e 897 (M+H)$^+$.

EXAMPLE 27

Hpa(SO$_3$H)-Met-Gly-Trp-Met-DAsp-Phe-NH$_2$

Hpa-Met-Gly-Trp-Met-DAsp-Phe-NH$_2$ (the product of Example 23, 114 mg) was dissolved in pyridine (1.4 ml) and sulphur trioxide pyridine complex (130 mg) was added. The reaction was stirred for 2 hours then an additional 80 mg of sulphur trioxide pyridine complex was added. After 4 hours the reaction was diluted with 5% NH$_4$OH (20 ml) and concentrated to dryness. The crude residue was purified by chromatography on SM-2, ODS-3, SM-2 sequentially according to Table 2, step 18. The resulting product was freeze dried from 0.1M NH$_3$ to give the title compound (89 mg). Amino acid analysis following acid decomposition gave Asp 1.03 (1), Gly 1.11 (1), Met 1.83 (2), Phe 1.04 (1), Trp 0.59 (1), NH$_3$ 2.2. MS (FAB): m/e 997 (M–H)$^-$.

EXAMPLE 28

Hpa(SO$_3$H)-Ahx-Gly-Trp-Ahx-MeAsp-Phe-NH$_2$ (SEQ ID NO 17)

Hpa-Ahx-Gly-Trp-Ahx-MeAsp-Phe-NH$_2$ (the product of Example 25, 55 mg) was sulphated essentially according to the method of Example 27 to give purified title compound (15 mg). Amino acid analysis following acid decomposition gave MeAsp 1.07 (1), Gly 1.04 (1), Ahx 1.90 (2), Phe 0.98 (1), Trp 0.61 (1), NH$_3$ 0.79. MS (FAB): m/e 975 (M–H)$^-$.

EXAMPLE 29

Hpa(SO₃H)-Ile-Gly-Trp-Ile-DAsp-MePhe-NH₂

Hpa-Ile-Gly-Trp-Ile-DAsp-MePhe-NH₂ (the product of Example 26, 58 mg) was sulphated essentially according to the method of Example 27 to give purified title compound (16 mg). Amino acid analysis following acid decomposition gave Asp 1.08 (1), Gly 1.08 (1), Ile 1.97 (2), MePhe 0.87 (1), Trp 0.75 (1) NH₃ 1.39. MS (FAB): m/e 975 (M–H)⁻. cl

EXAMPLE 30

Hpa-met-Gly-Trp-Met-Asp-MePhe-NH₂ (SEQ ID NO 18)

The title compound was prepared following the method of Table 2, sequentially coupling Fmoc-MePhe-OH, Fmoc-Asp(OtBu)-OH, Fmoc-met-OH, Fmoc-Trp-OH, Fmoc-Gly-OH, Fmoc-Met-OH and Hpa-OSu. Amino acid analysis following acid decomposition gave Asp 1.06 (1), Gly 1.04 (1), MePhe 1.00 (1), Met 1.90 (2), Trp 0.84 (1), NH₃ 0.51. MS (FAB): m/e 931 (M–H)⁻.

EXAMPLE 31

Hpa-Ahx-Gly-Trp-Ahx-DAsp-MePhe-NH₂

PAL resin was sequentially coupled according to Table 2 with Fmoc-MePhe-OH, Fmoc-DAsp(OtBu)-OH, Fmoc-Ahx-OH, Fmoc-Trp-OH, Fmoc-Gly-OH, Fmoc-Ahx-OH and Hpa-OSu, to give the title compound. Amino acid analysis following acid decomposition gave Asp 1.03 (1), Gly 1.04 (1), Ahx 1.95 (2), MePhe 0.99 (1), Trp 0.77 (1), NH₃ 0.94. MS (FAB): m/e 895 (M–H)⁻.

EXAMPLE 32

Hpa-Ahx-Gly-Trp-Ile-DAsp-Phe-NH₂

PAL resin was sequentially coupled according to Table 2 with Fmoc-Phe-OH, Fmoc-DAsp(OtBu)-OH, Fmoc-Ile-OH, Fmoc-Trp-OH, Fmoc-Gly-OH, Fmoc-Ahx-OH and Hpa-OSu, to give the title compound. Amino acid analysis following acid decomposition gave Asp 1.03 (1), Gly 1.04 (1), Ahx 0.96 (1), Ile 0.98 (1), Phe 1.00 (1), Trp 0.67 (1), NH₃ 0.99. MS (FAB): m/e 881 (M–H)⁻.

EXAMPLE 33

Hpa-Ahx-Gly-Trp-Ile-MeAsp-Phe-NH₂ (SEQ ID NO 19)

PAL resin was sequentially coupled according to Table 2 with Fmoc-Phe-OH, Fmoc-MeAsp(OtBu)-OH, Fmoc-Ile-OH, Fmoc-Trp-OH, Fmoc-Gly-OH, Fmoc-Ahx-OH and Hpa-OSu, to give the title compound. Amino acid analysis following acid decomposition gave MeAsp 1.19 (1), Gly 1.00 (1), Ahx 1.02 (1), Phe 0.91 (1), Ile 0.89 (1), Trp 0.65 (1), NH₃ 0.60. MS (FAB): m/e 895 (M–H)⁻.

EXAMPLE 34

Hpa-Ahx-Gly-Trp-Ile-Asp-MePhe-NH₂ (SEQ ID NO 20)

PAL resin was sequentially coupled according to Table 2 with Fmoc-MePhe-OH, Fmoc-Asp(OtBu)-OH, Fmoc-Ile-OH, Fmoc-Trp-OH, Fmoc-Gly-OH, Fmoc-Ahx-OH and Hpa-OSu, to give the title compound. Amino acid analysis following acid decomposition gave Asp 1.10 (1), Gly 1.09 (1), Ahx 1.06 (1), Ile 1.05 (1), MePhe 0.71 (1), Trp 0.76 (1), NH₃ 0.80. MS (FAB): m/e 895 (M–H)⁻.

EXAMPLE 35

Hpa(SO₃H)-Ahx-Gly-Trp-Ile-DAsp-Phe-NH₂

Hpa(SO₃H)-Ahx-Gly-Trp-Ile-DAsp-Phe-NH₂

Hpa-Ahx-Gly-Trp-Ile-DAsp-Phe-NH₂ (the product of Example 32, 41 mg) prepared according to Table 2 was sulphated essentially according to the method of Example 27 to give purified title compound (22 mg). Amino acid analysis following acid decomposition gave Asp 1.07 (1), Gly 1.04 (1), Ile 0.97 (1), Phe 0.80 (1), Trp 0.46 (1) NH₃ 1.88. MS (FAB): m/e 961 (M–H)⁻.

EXAMPLE 36

Hpa-Met-Gly-Trp-Met-Asp(OBn)-MePhe-NH₂ (SEQ ID NO 21)

By following essentially the procedures of Table 2 and sequentially coupling with Fmoc-MePhe-OH, Fmoc-Asp(OBn)-OH, Fmoc-Met-OH, Fmoc-Trp-OH, Fmoc-Gly-OH, Fmoc-Met-OH and Hpa-OSu, the title compound was prepared. MS (FAB): m/e 1023 (M+H)⁺.

EXAMPLE 37

Hpa(SO₃H)-Met-Gly-Trp-Met-Asp(OBn)-MePhe-NH₂ (SEQ ID NO 22)

Hpa-Met-Gly-Trp-Met-Asp(OBn)-MePhe-NH₂ (the product of Example 36) was sulphated essentially according to the procedures of Example 2 to give the purified title compound. Amino acid analysis following acid decomposition gave Asp 1.07 (1), Gly 0.99 (1), Met 1.91 (2), MePhe 1.02 (1), Trp 0.47 (1). MS (FAB): m/e 1101 (M–H)⁻.

EXAMPLE 38

Hpa-Ahx-Gly-Trp-Ile-DAsp-MePhe-NH₂

By following essentially the procedure of Table 2 and sequentially coupling Fmoc-MePhe-OH, Fmoc-DAsp(OtBu)-OH, Fmoc-Ile-OH, Fmoc-Trp-OH, Fmoc-Gly-OH, Fmoc-Ahx-OH and Hpa-OSu, the title compound was prepared. Amino Acid analysis following acid decomposition gave Asp 0.96 (1), Gly 1.04 (1), Ile 0.96 (1), MePhe 1.07 (1), Ahx 0.98 (1), Trp 0.61 (1), NH₃ 0.89. MS (FAB): m/e 895 (M–H)⁻.

EXAMPLE 39

Hpa(SO₃H)-Ahx-Gly-Trp-Ile-DAsp-MePhe-NH₂

Hpa-Ahx-Gly-Trp-Ile-DAsp-MePhe-NH₂ (the product of Example 38) was sulphated essentially according to the procedures of Example 27 to give the title compound. Amino Acid analysis following acid decomposition gave Asp 0.98 (1), Gly 1.07 (1), Ile 0.95 (1), MePhe 1.41 (1), Ahx 0.81 (1), MS (FAB): m/e 975 (M–H)⁻, m/e 895 (M–SO₃H)⁻.

EXAMPLE 40

Hpa(SO₃H)-Ahx-Gly-Trp-Ile-Asp-MePhe-NH₂
(SEQ ID NO 23)

Hpa-Ahx-Gly-Trp-Ile-Asp-MePhe-NH₂ (the product of Example 34) was sulphated essentially according to the procedures of Example 27 to give the title compound. Amino Acid analysis following acid decomposition gave Asp 0.98 (1), Gly 1.08 (1), Ile 0.96 (1), MePhe 1.55 (1), Ahx 0.84 (1). MS (FAB): m/e 975 (M–H)⁻, m/e 895 (M–SO₃H)⁻.

EXAMPLE 41

Hpa(SO₃H)-Ahx-Gly-Trp-Ahx-DAsp-MePhe-NH₂

Hpa-Ahx-Gly-Trp-Ahx-DAsp-MePhe-NH₂ (the product of Example 31) was sulphated essentially according to the procedures of Example 27 to give the title compound. Amino Acid analysis following acid decomposition gave Asp 1.00 (1), Gly 0.98 (1), MePhe 1.10 (1), Ahx 1.93 (2), Trp 0.96 (1), NH₃ 0.30. MS (FAB): m/e 975 (M–H)⁻.

EXAMPLE 42

Hpa-Ile-Gly-Trp-Ile-DAsp-Phe-NH₂

By following essentially the procedure of Table 2 and sequentially coupling Fmoc-Phe-OH, Fmoc-DAsp(OtBu)-OH, Fmoc-Ile-OH, Fmoc-Trp-OH, Fmoc-Gly-OH, Fmoc-Ile-OH and Hpa-OSu, the title compound was prepared. Amino Acid analysis following acid decomposition gave Asp 1.02 (1), Gly 1.03 (1), Phe 1.01 (1), Ile 1.94 (2), Trp 0.72 (1), NH₃ 0.85. MS (FAB): m/e 881 (M–H)⁻.

EXAMPLE 43

Hpa(SO₃H)-Ile-Gly-Trp-Ile-DAsp-Phe-NH₂

Hpa-Ile-Gly-Trp-Ile-DAsp-Phe-NH₂ (the product of Example 42) was sulphated essentially according to the procedures of Example 27 to give the title compound. Amino Acid analysis following acid decomposition gave Asp 0.92 (1), Gly 1.03 (1), Phe 0.99 (1), Ile 1.93 (2). MS (FAB): m/e 961 (M–H⁻.

EXAMPLE 44

Hpa-Ahx-Gly-Trp-Phe-DAsp-MePhe-NH₂

By following essentially the procedure of Table 2 and sequentially coupling Fmoc-MePhe-OH, Fmoc-DAsp(OtBu)-OH, Fmoc-Phe-OH, Fmoc-Trp-OH, Fmoc-Gly-OH, Fmoc-Ahx-OH and Hpa-OSu, the title compound was prepared. Amino Acid analysis following acid decomposition gave Asp 1.01 (1), Gly 0.99 (1), MePhe 1.06 (1), Ahx 1.02 (1), Trp 1.06 (1), Phe 0.94 (1), NH₃ 0.82. MS (FAB): m/e 931 (M–H)⁻.

EXAMPLE 45

Hpa(SO₃H)-Ahx-Gly-Trp-Phe-DAsp-MePhe-NH₂

Hpa-Ahx-Gly-Trp-Phe-DAsp-MePhe-NH₂ (the product of Example 44) was sulphated essentially according to the procedures of Example 27 to give the title compound. Amino acid analysis following acid decomposition gave Asp 0.98 (1), Gly 1.06 (1), MePhe 0.97 (1), Ahx 0.95 (1), Trp 0.61 (1), Phe 1.04 (1), NH₃ 1.10. MS (FAB): m/e 1009 (M–H)⁻, m/e 929 (M–SO₃H)⁻.

EXAMPLE 46

Hpa(SO₃H)-Ahx-Gly-Trp-Ahx-DAsp-Phe-NH₂

Hpa-Ahx-Gly-Trp-Ahx-DAsp-Phe-NH₂ was prepared by the method of Table 2, and sulphated essentially according to the procedures of Example 27 to give the title compound. Amino Acid analysis following acid decomposition gave Asp 1.02 (1), Gly 1.05 (1), Phe 1.02 (1), Ahx 1.92 (2), Trp 0.81 (1), NH₃ 1.48. MS (FAB): m/e 961 (M–H)⁻, 881 (M–SO₃H)⁻.

EXAMPLE 47

Hpa(SO₃H)-Ahx-Gly-Trp-Ile-MeAsp-MePhe-NH₂
(SEQ ID NO 24)

Hpa-Ahx-Gly-Trp-Ile-MeAsp-MePhe-NH₂ (SEQ ID NO 25) was prepared by the method of Table 2, and sulphated essentially according to the procedures of Example 27 to give the title compound. Amino Acid analysis following acid decomposition gave MeAsp 0.92 (1), Gly 1.00 (1), MePhe 1.29 (1), Ahx 0.77 (1), Ile 1.02 (1). MS (FAB): m/e 989 (M–H)⁻, 909 (M–SO₃H)⁻.

EXAMPLE 48

Hpa(SO₃H)-Ile-Gly-Trp-Ile-MeAsp-Phe-NH₂ (SEQ ID NO 26)

Hpa-Ile-Gly-Trp-Ile-MeAsp-Phe-NH₂ (SEQ ID NO 27) was prepared by the method of Table 2, and sulphated essentially according to the procedures of Example 27 to give the title compound. Amino Acid analysis following acid decomposition gave MeAsp 1.11 (1), Gly 1.00 (1), Phe 1.06 (1), Ile 1.83 (2), Trp 0.73 (1), NH₃ 1.48. MS (FAB): m/e 975 (M–H)⁻, 897 (M–SO₃H)⁻.

EXAMPLE 49

Hpa-Ahx-Gly-Trp-Ahx-MeDAsp-Phe-NH₂

By following essentially the procedure of Table 2 and sequentially coupling Fmoc-Phe-OH, Fmoc-MeDAsp(OtBu)-OH, Fmoc-Ahx-OH, Fmoc-Trp-OH, Fmoc-Gly-OH, Fmoc-Ahx-OH and Hpa-OSu, the title compound was prepared. Amino Acid analysis following acid decomposition gave MeAsp 0.78 (1), Gly 1.10 (1), Phe 1.05 (1), Ahx 2.07 (2), Trp 0.76 (1), NH₃ 0.71. MS (FAB): m/e 895 (M–H)⁻.

EXAMPLE 50

Hpa(SO₃H)-Ahx-Gly-Trp-Ahx-MeDAsp-Phe-NH₂

Hpa-Ahx-Gly-Trp-Ahx-MeDAsp-Phe-NH₂ (the product of Example 49) was sulphated essentially according to the procedures of Example 27 to give the title compound. Amino Acid analysis following acid decomposition gave MeAsp 1.00 (1), Gly 1.02 (1), Phe 1.06 (1), Ahx 1.91 (2), Trp 0.86 (1), NH₃ 1.48. MS (FAB): m/e 975 (M–H)⁻, m/e 896 (M–SO₃H)⁻.

EXAMPLE 51

Hpa-Ahx-Gly-Trp-Ahx-MeAsp-MePhe-NH$_2$ (SEQ ID NO 28)

By following essentially the procedure of Table 2 and sequentially coupling Fmoc-MePhe-OH, Fmoc-MeAsp(OtBu)-OH, Fmoc-Ahx-OH, Fmoc-Trp-OH, Fmoc-Gly-OH, Fmoc-Ahx-OH and Hpa-OSu, the title compound was prepared. Amino Acid analysis following acid decomposition gave MeAsp 1.01 (1), Gly 1.05 (1), MePhe 0.91 (1), Ahx 2.02 (2), Trp 0.84 (1), NH$_3$ 0.82. MS (FAB): m/e 909 (M−H)$^-$.

EXAMPLE 52

Hpa-Ahx-Gly-Trp-Lys(Tac)-Asp-MePhe-NH$_2$ (SEQ ID NO 29)

Following the procedure of Table 2, Fmoc-MePhe-OH, Fmoc-Asp(OtBu)-OH, Fmoc-Ahx-OH, Fmoc-Trp-OH, Fmoc-Gly-OH, Fmoc-Lys(Boc)-OH and Hpa-OSu were sequentially coupled to the Rink amide resin. Following removal of the peptide from the resin using standard procedures the 2-methylphenylacetamide group was added to the ε-amino of Lys using o-tolylisocyanate. Amino Acid analysis following acid decomposition gave Asp 1.01 (1), Gly 1.03 (1), MePhe 0.98 (1), Lys 0.94 (1), Ahx 1.04 (1), Trp 0.96 (1). MS (FAB): m/e 1046 (M−H)$^+$.

EXAMPLE 53

Hpa(SO$_3$H)-Ahx-Gly-Trp-Lys(Tac)-Asp-MePhe-NH$_2$ (SEQ ID NO 30)

Hpa(SO$_3$H)-Ahx-Gly-Trp-Lys(Tac)-Asp-MePhe-NH$_2$ (the product of Example 52) was sulphated according to the procedures of Example 27 to give the title compound. Amino Acid analysis following acid decomposition gave Asp 1.01 (1), Gly 1.04 (1), MePhe 0.92 (1), Lys 0.93 (1), Ahx 1.10 (1), Trp 0.84 (1). MS (FAB): m/e 1123 (M−H)$^-$.

EXAMPLE 54

Hpa-Ahx-Gly-Trp-Ahx-Asp-MePhe-NH$_2$ (SEQ ID NO 31)

Following the procedure of Table 2 and sequentially coupling Fmoc-MePhe-OH, Fmoc-Asp(OtBu)-OH, Fmoc-Ahx-OH, Fmoc-Trp-OH, Fmoc-Gly-OH, Fmoc-Ahx-OH and Hpa-OSu, to the resin, the title compound was prepared. Amino Acid analysis following acid decomposition gave Asp 1.00 (1), Gly 1.02 (1), MePhe 1.05 (1), Ahx 2.1 (2), Trp 0.53 (1), NH$_3$ 0.69. MS (FAB): m/e 897 (M+H)$^+$.

EXAMPLE 55

Hpa-Ahx-Sar-Trp-Ahx-Asp-MePhe-NH$_2$ (SEQ ID NO 32)

Following the procedure of Table 2 and sequentially coupling Fmoc-MePhe-OH, Fmoc-Asp(OtBu)-OH, Fmoc-Ahx-OH, Fmoc-Trp-OH, Fmoc-Sar-OH, Fmoc-Ahx-OH and Hpa-OSu, to the resin, the title compound was prepared. Amino Acid analysis following acid decomposition gave Asp 0.93 (1), Sar 1.12 (1), MePhe 0.95 (1), Ahx 1.99 (2), Trp 1.06 (1), HN$_3$ 0.88. MS (FAB): m/e 909 (M−H$^-$.

EXAMPLE 56

Hpa(SO$_3$H)-Ahx-Sar-Trp-Ahx-Asp-MePhe-NH$_2$ (SEQ ID NO 33)

Hpa-Ahx-Sar-Trp-Ahx-Asp-MePhe-NH$_2$ (the product of Example 55) was sulphated according to the procedures of Example 27 to give the title compound. Amino Acid analysis following acid decomposition Asp 1.04 (1), Sar 0.87 (1), MePhe 0.86 (1), Ahx 2.23 (2), Trp 0.89 (1), NH$_3$ 1.31, MS (FAB) me/ 989 (M−H)$^-$.

EXAMPLE 57

The compound of Example 49 was tested in Test B above, and found to bind to CCK-A receptors with a binding constant ($K_i$) of 0.03 nM.

---

Sequence Listing (Total of 33 sequences)

(1) INFORMATION FOR SEQ ID NO 1:

(i)    SEQUENCE CHARACTERISTICS
        (A)    LENGTH: 6 residues
        (B)    TYPE: amino acid
        (D)    TOPOLOGY: linear (ii)   MOLECULE TYPE: peptide (ix)   FEATURE:
        (A)    NAME/KEY: misc-feature
        (B)    LOCATION: 1
        (D)    OTHER INFORMATION: Xaa is N-[2-(O-sulpho-4- oxyphenyl)ethanoyl]-Met (ix)   FEATURE:
        (A)    NAME/KEY: misc-feature
        (B)    LOCATION: 6
        (D)    OTHER INFORMATION: Xaa is phenylalanine amide (xi)   SEQUENCE DESCRIPTION: SEQ ID NO 1

Xaa Gly Trp Met Asp Xaa
1                  5

(2) INFORMATION FOR SEQ ID NO 2:

(i)    SEQUENCE CHARACTERISTICS
        (A)    LENGTH: 6 residues
        (B)    TYPE: amino acid
        (D)    TOPOLOGY: linear (ii)   MOLECULE TYPE: peptide (ix)   FEATURE:
        (A)    NAME/KEY: misc-feature
        (B)    LOCATION: 1
        (D)    OTHER INFORMATION: Xaa is N-[2-(O-sulpho-4-oxyphenyl)ethanoyl]-Ala (ix)   FEATURE:
        (A)    NAME/KEY: misc-feature
        (B)    LOCATION: 6
        (D)    OTHER INFORMATION: Xaa is phenylalanine amide (xi)   SEQUENCE DESCRIPTION: SEQ ID NO 2

Xaa Gly Trp Met Asp Xaa
1                  5

(3) INFORMATION FOR SEQ ID NO 3:

(i)    SEQUENCE CHARACTERISTICS
        (A)    LENGTH: 6 residues
        (B)    TYPE: amino acid
        (D)    TOPOLOGY: linear

```
        (ii)  MOLECULE TYPE: peptide (ix)  FEATURE:
              (A)  NAME/KEY: misc-feature
              (B)  LOCATION: 1
              (D)  OTHER INFORMATION: Xaa is
                   N-[2-(O-sulpho-4-oxyphenyl)ethanoyl]-Met (ix)  FEATURE:
              (A)  NAME/KEY: misc-feature
              (B)  LOCATION: 6
              (D)  OTHER INFORMATION: Xaa is N-methyl
                   phenylalanine amide (xi)  SEQUENCE DESCRIPTION: SEQ ID NO 3

Xaa Gly Trp Met Asp Xaa
         1                   5

(4) INFORMATION FOR SEQ ID NO 4:

(i)   SEQUENCE CHARACTERISTICS
              (A)  LENGTH: 6 residues
              (B)  TYPE: amino acid
              (D)  TOPOLOGY: linear (ii)  MOLECULE TYPE: peptide (ix)  FEATURE:
              (A)  NAME/KEY: misc-feature
              (B)  LOCATION: 1
              (D)  OTHER INFORMATION: Xaa is
                   N-[2-(O-sulpho-4-oxyphenyl)ethanoyl]-Ala (ix)  FEATURE:
              (A)  NAME/KEY: misc-feature
              (B)  LOCATION: 6
              (D)  OTHER INFORMATION: Xaa is
                   N-methyl phenylalanine amide (xi)  SEQUENCE DESCRIPTION: SEQ ID NO 4

Xaa Gly Trp Met Asp Xaa
         1                   5

(5) INFORMATION FOR SEQ ID NO 5:

(i)   SEQUENCE CHARACTERISTICS
              (A)  LENGTH: 6 residues
              (B)  TYPE: amino acid
              (D)  TOPOLOGY: linear (ii)  MOLECULE TYPE: peptide (ix)  FEATURE:

(A)  NAME/KEY: misc-feature
              (B)  LOCATION: 1
              (D)  OTHER INFORMATION: Xaa is
                   N-[2-(O-sulpho-4-oxyphenyl)ethanoyl]-Met (ix)  FEATURE:
              (A)  NAME/KEY: misc-feature
              (B)  LOCATION: 6
              (D)  OTHER INFORMATION: Xaa is
                   N-methyl phenylalanine amide (xi)  SEQUENCE DESCRIPTION: SEQ ID NO 5

Xaa Gly Ala Met Asp Xaa
         1                   5

(6) INFORMATION FOR SEQ ID NO 6:

(i)   SEQUENCE CHARACTERISTICS
              (A)  LENGTH: 6 residues
              (B)  TYPE: amino acid
              (D)  TOPOLOGY: linear (ii)  MOLECULE TYPE: peptide (ix)  FEATURE:
              (A)  NAME/KEY: misc-feature
              (B)  LOCATION: 1
              (D)  OTHER INFORMATION: Xaa is
                   N-[2-(O-sulpho-4-oxyphenyl)ethanoyl]-Met (ix)  FEATURE:
              (A)  NAME/KEY: misc-feature
              (B)  LOCATION: 6
              (D)  OTHER INFORMATION: Xaa is
                   N-methyl phenylalanine amide (xi)  SEQUENCE DESCRIPTION: SEQ ID NO 6

Xaa Gly Trp Ala Asp Xaa
         1                   5

(7) INFORMATION FOR SEQ ID NO 7:

(i)   SEQUENCE CHARACTERISTICS
              (A)  LENGTH: 6 residues
              (B)  TYPE: amino acid
              (D)  TOPOLOGY: linear (ii)  MOLECULE TYPE: peptide (ix)  FEATURE:
              (A)  NAME/KEY: misc-feature
              (B)  LOCATION: 1
              (D)  OTHER INFORMATION: Xaa is
                   N-[2-(O-sulpho-4-oxyphenyl)ethanoyl]-Met (ix)  FEATURE:
              (A)  NAME/KEY: misc-feature
              (B)  LOCATION: 6
              (D)  OTHER INFORMATION: Xaa is
                   N-methyl phenylalanine amide (xi)  SEQUENCE DESCRIPTION: SEQ ID NO 7

Xaa Gly Trp Met Ala Xaa
         1                   5

(8) INFORMATION FOR SEQ ID NO 8:

(i)   SEQUENCE CHARACTERISTICS
              (A)  LENGTH: 6 residues
              (B)  TYPE: amino acid
              (D)  TOPOLOGY: linear (ii)  MOLECULE TYPE: peptide (ix)  FEATURE:
              (A)  NAME/KEY: misc-feature
              (B)  LOCATION: 1
              (D)  OTHER INFORMATION: Xaa is
                   N-[2-(O-sulpho-4-oxyphenyl)ethanoyl]-Ala (ix)  FEATURE:
              (A)  NAME/KEY: misc-feature
              (B)  LOCATION: 6
              (D)  OTHER INFORMATION: Xaa is
                   N-methyl phenylalanine amide (xi)  SEQUENCE DESCRIPTION: SEQ ID NO 8

Xaa Gly Trp Ala Asp Xaa
         1                   5

(9) INFORMATION FOR SEQ ID NO 9:

(i)   SEQUENCE CHARACTERISTICS
              (A)  LENGTH: 6 residues
              (B)  TYPE: amino acid
              (D)  TOPOLOGY: linear (ii)  MOLECULE TYPE: peptide (ix)  FEATURE:
              (A)  NAME/KEY: misc-feature
```

(B) LOCATION: 1
        (D) OTHER INFORMATION: Xaa is
            N-[2-(O-sulpho-4-oxyphenyl)ethanoyl]-Nle (ix) FEATURE:
        (A) NAME/KEY: misc-feature
        (B) LOCATION: 4
        (D) OTHER INFORMATION: Leu is Nle (ix) FEATURE:
        (A) NAME/KEY: misc-feature
        (B) LOCATION: 6
        (D) OTHER INFORMATION: Xaa is
            N-methyl phenylalanine amide (xi) SEQUENCE DESCRIPTION: SEQ ID NO 9

Xaa Gly Trp Leu Asp Xaa
 1                   5

(10) INFORMATION FOR SEQ ID NO 10:

(i) SEQUENCE CHARACTERISTICS
        (A) LENGTH: 6 residues
        (B) TYPE: amino acid
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION: Xaa is
            N-[2-(O-sulpho-4-oxyphenyl)ethanoyl]-Ile (ix) FEATURE:
        (A) NAME/KEY: misc-feature
        (B) LOCATION: 6
        (D) OTHER INFORMATION: Xaa is
            N-methyl phenylalanine amide (xi) SEQUENCE DESCRIPTION: SEQ ID NO 10

Xaa Gly Trp Ile Asp Xaa
 1                   5

(11) INFORMATION FOR SEQ ID NO 11:

(i) SEQUENCE CHARACTERISTICS
        (A) LENGTH: 6 residues
        (B) TYPE: amino acid
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION: Xaa is
            N-[2-(O-sulpho-4-oxyphenyl)ethanoyl]-Ile (ix) FEATURE:
        (A) NAME/KEY: misc-feature
        (B) LOCATION: 4
        (D) OTHER INFORMATION: Leu is Nle (ix) FEATURE:
        (A) NAME/KEY: misc-feature
        (B) LOCATION: 6
        (D) OTHER INFORMATION: Xaa is
            N-methyl phenylalanine amide (xi) SEQUENCE DESCRIPTION: SEQ ID NO 11

Xaa Gly Trp Leu Asp Xaa
 1                   5

(12) INFORMATION FOR SEQ ID NO 12:

(i) SEQUENCE CHARACTERISTICS
        (A) LENGTH: 6 residues
        (B) TYPE: amino acid
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION: Xaa is
            N-[2-(O-sulpho-4-oxyphenyl)ethanoyl]-Met (ix) FEATURE:
        (A) NAME/KEY: misc-feature
        (B) LOCATION: 6
        (D) OTHER INFORMATION: Xaa is
            N-methyl phenylalanine amide (xi) SEQUENCE DESCRIPTION: SEQ ID NO 12

Xaa Ala Trp Met Asp Xaa
 1                   5

(13) INFORMATION FOR SEQ ID NO 13:

(i) SEQUENCE CHARACTERISTICS
        (A) LENGTH: 6 residues
        (B) TYPE: amino acid
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION: Xaa is
            N-[2-(O-sulpho-4-oxyphenyl)ethanoyl]-Met (ix) FEATURE:
        (A) NAME/KEY: misc-feature
        (B) LOCATION: 2
        (D) OTHER INFORMATION: Ala is
            β-alanine (ix) FEATURE:
        (A) NAME/KEY: misc-feature
        (B) LOCATION: 6
        (D) OTHER INFORMATION: Xaa is
            N-methyl phenylalanine amide (xi) SEQUENCE DESCRIPTION: SEQ ID NO 13

Xaa Ala Trp Met Asp Xaa
 1                   5

(14) INFORMATION FOR SEQ ID NO 14:

(i) SEQUENCE CHARACTERISTICS
        (A) LENGTH: 6 residues
        (B) TYPE: amino acid
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION: Xaa is
            N-[2-(O-sulpho-4-oxyphenyl)ethanoyl]-Nle (ix) FEATURE:
        (A) NAME/KEY: misc-feature
        (B) LOCATION: 4
        (D) OTHER INFORMATION: Leu is Nle (ix) FEATURE:
        (A) NAME/KEY: misc-feature
        (B) LOCATION: 6
        (D) OTHER INFORMATION: Xaa is
            phenylalanine amide -continued (xi) SEQUENCE DESCRIPTION: SEQ ID NO 14

Xaa Gly Trp Leu Asp Xaa
1               5

(15) INFORMATION FOR SEQ ID NO 15:

(i) SEQUENCE CHARACTERISTICS
  (A) LENGTH: 6 residues
  (B) TYPE: amino acid
  (D) TOPOLOGY: linear (ii) MOLECULE TYPE: peptide (ix) FEATURE:
  (A) NAME/KEY: misc-feature
  (B) LOCATION: 1
  (D) OTHER INFORMATION: Xaa is N-[2-(4-hydroxyphenyl)ethanoyl]-Nle (ix) FEATURE:
  (A) NAME/KEY: misc-feature
  (B) LOCATION: 4
  (D) OTHER INFORMATION: Leu is Nle (ix) FEATURE:
  (A) NAME/KEY: misc-feature
  (B) LOCATION: 6
  (D) OTHER INFORMATION: Xaa is phenylalanine amide (xi) SEQUENCE DESCRIPTION: SEQ ID NO 15

Xaa Gly Trp Leu Asp Xaa
1               5

(16) INFORMATION FOR SEQ ID NO 16:

(i) SEQUENCE CHARACTERISTICS
  (A) LENGTH: 6 residues
  (B) TYPE: amino acid
  (D) TOPOLOGY: linear (ii) MOLECULE TYPE: peptide (ix) FEATURE:
  (A) NAME/KEY: misc-feature
  (B) LOCATION: 1
  (D) OTHER INFORMATION: Xaa is N-[2-(4-hydroxyphenyl)ethanoyl]-Nle (ix) FEATURE:
  (A) NAME/KEY: misc-feature
  (B) LOCATION: 4
  (D) OTHER INFORMATION: Leu is Nle (ix) FEATURE:
  (A) NAME/KEY: misc-feature
  (B) LOCATION: 5
  (D) OTHER INFORMATION: Xaa is N-methyl aspartic acid (ix) FEATURE:
  (A) NAME/KEY: misc-feature
  (B) LOCATION: 6
  (D) OTHER INFORMATION: Xaa is phenylalanine amide (xi) SEQUENCE DESCRIPTION: SEQ ID NO 16

Xaa Gly Trp Leu Xaa Xaa
1               5

(17) INFORMATION FOR SEQ ID NO 17:

(i) SEQUENCE CHARACTERISTICS
  (A) LENGTH: 6 residues
  (B) TYPE: amino acid
  (D) TOPOLOGY: linear (ii) MOLECULE TYPE: peptide (ix) FEATURE:
  (A) NAME/KEY: misc-feature
  (B) LOCATION: 1
  (D) OTHER INFORMATION: Xaa is N-[2-(O-sulpho-4-oxyphenyl)ethanoyl]-Nle (ix) FEATURE:
  (A) NAME/KEY: misc-feature
  (B) LOCATION: 4
  (D) OTHER INFORMATION: Leu is Nle (ix) FEATURE:
  (A) NAME/KEY: misc-feature
  (B) LOCATION: 5
  (D) OTHER INFORMATION: Xaa is N-methyl-Asp (ix) FEATURE:
  (A) NAME/KEY: misc-feature
  (B) LOCATION: 6
  (D) OTHER INFORMATION: Xaa is phenylalanine amide (xi) SEQUENCE DESCRIPTION: SEQ ID NO 17

Xaa Gly Trp Leu Xaa Xaa
1               5

(18) INFORMATION FOR SEQ ID NO 18:

(i) SEQUENCE CHARACTERISTICS
  (A) LENGTH: 6 residues
  (B) TYPE: amino acid
  (D) TOPOLOGY: linear (ii) MOLECULE TYPE: peptide (ix) FEATURE:
  (A) NAME/KEY: misc-feature
  (B) LOCATION: 1
  (D) OTHER INFORMATION: Xaa is N-[4-hydroxyphenyl)ethanoyl]-Met (ix) FEATURE:
  (A) NAME/KEY: misc-feature
  (B) LOCATION: 6
  (D) OTHER INFORMATION: Xaa is N-methyl-phenylalanine amide (xi) SEQUENCE DESCRIPTION: SEQ ID NO 18

Xaa Gly Trp Met Asp Xaa
1               5

(19) INFORMATION FOR SEQ ID NO 19:

(i) SEQUENCE CHARACTERISTICS
  (A) LENGTH: 6 residues
  (B) TYPE: amino acid
  (D) TOPOLOGY: linear (ii) MOLECULE TYPE: peptide (ix) FEATURE:
  (A) NAME/KEY: misc-feature
  (B) LOCATION: 1
  (D) OTHER INFORMATION: Xaa is N-[4-hydroxyphenyl)ethanoyl]-Nle (ix) FEATURE:
  (A) NAME/KEY: misc-feature
  (B) LOCATION: 5
  (D) OTHER INFORMATION: Xaa is N-methyl-Asp (ix) FEATURE:
  (A) NAME/KEY: misc-feature
  (B) LOCATION: 6
  (D) OTHER INFORMATION: Xaa is phenylalanine amide (xi) SEQUENCE DESCRIPTION: SEQ ID NO 19

Xaa Gly Trp Ile Xaa Xaa
1               5

(20) INFORMATION FOR SEQ ID NO 20:

(i) SEQUENCE CHARACTERISTICS
 (A) LENGTH: 6 residues
 (B) TYPE: amino acid
 (D) TOPOLOGY: linear (ii) MOLECULE TYPE: peptide (ix) FEATURE:
 (A) NAME/KEY: misc-feature
 (B) LOCATION: 1
 (D) OTHER INFORMATION: Xaa is N-[4-hydroxyphenyl)ethanoyl]-Nle (ix) FEATURE:
 (A) NAME/KEY: misc-feature
 (B) LOCATION: 6
 (D) OTHER INFORMATION: Xaa is N-methyl-phenylalanine amide (xi) SEQUENCE DESCRIPTION: SEQ ID NO 20

Xaa Gly Trp Ile Asp Xaa
1               5

(21) INFORMATION FOR SEQ ID NO 21:

(i) SEQUENCE CHARACTERISTICS
 (A) LENGTH: 6 residues
 (B) TYPE: amino acid
 (D) TOPOLOGY: linear (ii) MOLECULE TYPE: peptide (ix) FEATURE:
 (A) NAME/KEY: misc-feature
 (B) LOCATION: 1
 (D) OTHER INFORMATION: Xaa is N-[2-(4-hydroxyphenyl)ethanoyl]-Met (ix) FEATURE:
 (A) NAME/KEY: misc-feature
 (B) LOCATION: 5
 (D) OTHER INFORMATION: Xaa is Asp β-benzyl ester (ix) FEATURE:
 (A) NAME/KEY: misc-feature
 (B) LOCATION: 6
 (D) OTHER INFORMATION: Xaa is N-methyl-phenylalanine amide (xi) SEQUENCE DESCRIPTION: SEQ ID NO 21

Xaa Gly Trp Met Xaa Xaa
1               5

(22) INFORMATION FOR SEQ ID NO 22:

(i) SEQUENCE CHARACTERISTICS
 (A) LENGTH: 6 residues
 (B) TYPE: amino acid
 (D) TOPOLOGY: linear (ii) MOLECULE TYPE: peptide (ix) FEATURE:
 (A) NAME/KEY: misc-feature
 (B) LOCATION: 1
 (D) OTHER INFORMATION: Xaa is N-[2-(O-sulpho-4-oxyphenyl)ethanoyl]-Met (ix) FEATURE:
 (A) NAME/KEY: misc-feature
 (B) LOCATION: 5
 (D) OTHER INFORMATION: Xaa is Asp β-benzyl ester (ix) FEATURE:
 (A) NAME/KEY: misc-feature
 (B) LOCATION: 6
 (D) OTHER INFORMATION: Xaa is N-methyl-phenylalanine amide (xi) SEQUENCE DESCRIPTION: SEQ ID NO 22

Xaa Gly Trp Met Xaa Xaa
1               5

(23) INFORMATION FOR SEQ ID NO 23:

(i) SEQUENCE CHARACTERISTICS
 (A) LENGTH: 6 residues
 (B) TYPE: amino acid
 (D) TOPOLOGY: linear (ii) MOLECULE TYPE: peptide (ix) FEATURE:
 (A) NAME/KEY: misc-feature
 (B) LOCATION: 1
 (D) OTHER INFORMATION: Xaa is N-[O-sulpho-4-oxyphenyl)ethanoyl]-Nle (ix) FEATURE:
 (A) NAME/KEY: misc-feature
 (B) LOCATION: 6
 (D) OTHER INFORMATION: Xaa is N-methyl-phenylalanine amide (xi) SEQUENCE DESCRIPTION: SEQ ID NO 23

Xaa Gly Trp Ile Asp Xaa
1               5

(24) INFORMATION FOR SEQ ID NO 24:

(i) SEQUENCE CHARACTERISTICS
 (A) LENGTH: 6 residues
 (B) TYPE: amino acid
 (D) TOPOLOGY: linear (ii) MOLECULE TYPE: peptide (ix) FEATURE:
 (A) NAME/KEY: misc-feature
 (B) LOCATION: 1
 (D) OTHER INFORMATION: Xaa is N-[2-(O-sulpho-4-oxyphenyl)ethanoyl]-Nle (ix) FEATURE:
 (A) NAME/KEY: misc-feature
 (B) LOCATION: 5
 (D) OTHER INFORMATION: Xaa is N-methyl-Asp (ix) FEATURE:
 (A) NAME/KEY: misc-feature
 (B) LOCATION: 6
 (D) OTHER INFORMATION: Xaa is N-methyl-phenylalanine amide (xi) SEQUENCE DESCRIPTION: SEQ ID NO 24

Xaa Gly Trp Ile Xaa Xaa
1               5

(25) INFORMATION FOR SEQ ID NO 25:

(i) SEQUENCE CHARACTERISTICS
 (A) LENGTH: 6 residues
 (B) TYPE: amino acid
 (D) TOPOLOGY: linear (ii) MOLECULE TYPE: peptide (ix) FEATURE:
(A) NAME/KEY: misc-feature
(B) LOCATION: 1
(D) OTHER INFORMATION: Xaa is N-[2-(4-hydroxyphenyl)ethanoyl]-Nle (ix) FEATURE:
(A) NAME/KEY: misc-feature
(B) LOCATION: 5
(D) OTHER INFORMATION: Xaa is N-methyl-Asp (ix) FEATURE:
(A) NAME/KEY: misc-feature
(B) LOCATION: 6
(D) OTHER INFORMATION: Xaa is N-methyl-phenylalanine amide (xi) SEQUENCE DESCRIPTION: SEQ ID NO 25

Xaa Gly Trp Ile Xaa Xaa
1               5

(26) INFORMATION FOR SEQ ID NO 26:

(i) SEQUENCE CHARACTERISTICS
(A) LENGTH: 6 residues
(B) TYPE: amino acid
(D) TOPOLOGY: linear (ii) MOLECULE TYPE: peptide (ix) FEATURE:
(A) NAME/KEY: misc-feature
(B) LOCATION: 1
(D) OTHER INFORMATION: Xaa is N-[2-(O-sulpho-4-oxyphenyl)ethanoyl]-Ile (ix) FEATURE:
(A) NAME/KEY: misc-feature
(B) LOCATION: 5
(D) OTHER INFORMATION: Xaa is N-methyl-Asp (ix) FEATURE:
(A) NAME/KEY: misc-feature
(B) LOCATION: 6
(D) OTHER INFORMATION: Xaa is phenylalanine amide (xi) SEQUENCE DESCRIPTION: SEQ ID NO 26

Xaa Gly Trp Ile Xaa Xaa
1               5

(27) INFORMATION FOR SEQ ID NO 27:

(i) SEQUENCE CHARACTERISTICS
(A) LENGTH: 6 residues
(B) TYPE: amino acid
(D) TOPOLOGY: linear (ii) MOLECULE TYPE: peptide (ix) FEATURE:
(A) NAME/KEY: misc-feature
(B) LOCATION: 1
(D) OTHER INFORMATION: Xaa is N-[2-(4-hydroxyphenyl)ethanoyl]-Ile (ix) FEATURE:
(A) NAME/KEY: misc-feature
(B) LOCATION: 5
(D) OTHER INFORMATION: Xaa is N-methyl-Asp (ix) FEATURE:
(A) NAME/KEY: misc-feature
(B) LOCATION: 6
(D) OTHER INFORMATION: Xaa is phenylalanine amide (xi) SEQUENCE DESCRIPTION: SEQ ID NO 27

Xaa Gly Trp Ile Xaa Xaa
1               5

(28) INFORMATION FOR SEQ ID NO 28:

(i) SEQUENCE CHARACTERISTICS
(A) LENGTH: 6 residues
(B) TYPE: amino acid
(D) TOPOLOGY: linear (ii) MOLECULE TYPE: peptide (ix) FEATURE:
(A) NAME/KEY: misc-feature
(B) LOCATION: 1
(D) OTHER INFORMATION: Xaa is N-[2-(4-hydroxyphenyl)ethanoyl]-Nle (ix) FEATURE:
(A) NAME/KEY: misc-feature
(B) LOCATION: 4
(D) OTHER INFORMATION: Leu is Nle (ix) FEATURE:
(A) NAME/KEY: misc-feature
(B) LOCATION: 5
(D) OTHER INFORMATION: Xaa is N-methyl-Asp (ix) FEATURE:
(A) NAME/KEY: misc-feature
(B) LOCATION: 6
(D) OTHER INFORMATION: Xaa is N-methyl-phenylalanine amide (xi) SEQUENCE DESCRIPTION: SEQ ID NO 28

Xaa Gly Trp Leu Xaa Xaa
1               5

(29) INFORMATION FOR SEQ ID NO 29:

(i) SEQUENCE CHARACTERISTICS
(A) LENGTH: 6 residues
(B) TYPE: amino acid
(D) TOPOLOGY: linear (ii) MOLECULE TYPE: peptide (ix) FEATURE:
(A) NAME/KEY: misc-feature
(B) LOCATION: 1
(D) OTHER INFORMATION: Xaa is N-[2-(4-hydroxyphenyl)ethanoyl]-Nle (ix) FEATURE:
(A) NAME/KEY: misc-feature
(B) LOCATION: 4
(D) OTHER INFORMATION: Xaa is ε-N-[(2-methylphenyl)aminocarbonyl]-Lys (ix) FEATURE:
(A) NAME/KEY: misc-feature
(B) LOCATION: 6
(D) OTHER INFORMATION: Xaa is N-methyl-phenylalanine amide (xi) SEQUENCE DESCRIPTION: SEQ ID NO 29

Xaa Gly Trp Xaa Asp Xaa
1               5

(30) INFORMATION FOR SEQ ID NO 30:

(i) SEQUENCE CHARACTERISTICS (A)   LENGTH: 6 residues
        (B)   TYPE: amino acid
        (D)   TOPOLOGY: linear (ii)  MOLECULE TYPE: peptide (ix)  FEATURE:
        (A)   NAME/KEY: misc-feature
        (B)   LOCATION: 1
        (D)   OTHER INFORMATION: Xaa is
              N-[2-(O-sulpho-4-oxyphenyl)ethanoyl]-Nle (ix)  FEATURE:
        (A)   NAME/KEY: misc-feature
        (B)   LOCATION: 4
        (D)   OTHER INFORMATION: Xaa is
              ε-N-[(2-methylphenyl)aminocarbonyl]-Lys (ix)  FEATURE:
        (A)   NAME/KEY: misc-feature
        (B)   LOCATION: 6
        (D)   OTHER INFORMATION: Xaa is
              N-methyl-phenylalanine amide (xi)  SEQUENCE DESCRIPTION: SEQ ID NO 30

Xaa Gly Trp Xaa Asp Xaa
  1               5

(31) INFORMATION FOR SEQ ID NO 31:

(i)   SEQUENCE CHARACTERISTICS
        (A)   LENGTH: 6 residues
        (B)   TYPE: amino acid
        (D)   TOPOLOGY: linear (ii)  MOLECULE TYPE: peptide (ix)  FEATURE:
        (A)   NAME/KEY: misc-feature
        (B)   LOCATION: 1
        (D)   OTHER INFORMATION: Xaa is
              N-[2-(4-hydroxyphenyl)ethanoyl]-Nle (ix)  FEATURE:
        (A)   NAME/KEY: misc-feature
        (B)   LOCATION: 4
        (D)   OTHER INFORMATION: Leu is Nle (ix)  FEATURE:
        (A)   NAME/KEY: misc-feature
        (B)   LOCATION: 6
        (D)   OTHER INFORMATION: Xaa is
              N-methyl-phenylalanine amide (xi)  SEQUENCE DESCRIPTION: SEQ ID NO 31

Xaa Gly Trp Leu Asp Xaa
  1               5

(32) INFORMATION FOR SEQ ID NO 32:

(i)   SEQUENCE CHARACTERISTICS
        (A)   LENGTH: 6 residues
        (B)   TYPE: amino acid
        (D)   TOPOLOGY: linear (ii)  MOLECULE TYPE: peptide (ix)  FEATURE:
        (A)   NAME/KEY: misc-feature
        (B)   LOCATION: 1
        (D)   OTHER INFORMATION: Xaa is
              N-[2-(4-hydroxyphenyl)ethanoyl]-Nle (ix)  FEATURE:
        (A)   NAME/KEY: misc-feature
        (B)   LOCATION: 2
        (D)   OTHER INFORMATION: Gly is sarcosine (ix)  FEATURE:
        (A)   NAME/KEY: misc-feature
        (B)   LOCATION: 4
        (D)   OTHER INFORMATION: Leu is Nle (ix)  FEATURE:
        (A)   NAME/KEY: misc-feature
        (B)   LOCATION: 6
        (D)   OTHER INFORMATION: Xaa is
              N-methyl-phenylalanine amide (xi)  SEQUENCE DESCRIPTION: SEQ ID NO 32

Xaa Gly Trp Leu Asp Xaa
  1               5

(33) INFORMATION FOR SEQ ID NO 33:

(i)   SEQUENCE CHARACTERISTICS
        (A)   LENGTH: 6 residues
        (B)   TYPE: amino acid
        (D)   TOPOLOGY: linear (ii)  MOLECULE TYPE: peptide (ix)  FEATURE:
        (A)   NAME/KEY: misc-feature
        (B)   LOCATION: 1
        (D)   OTHER INFORMATION: Xaa is
              N-[2-(O-sulpho-4-oxyphenyl)ethanoyl]-Nle (ix)  FEATURE:
        (A)   NAME/KEY: misc-feature
        (B)   LOCATION: 2
        (D)   OTHER INFORMATION: Gly is sarcosine (ix)  FEATURE:
        (A)   NAME/KEY: misc-feature
        (B)   LOCATION: 4
        (D)   OTHER INFORMATION: Leu is Nle (ix)  FEATURE:
        (A)   NAME/KEY: misc-feature
        (B)   LOCATION: 6
        (D)   OTHER INFORMATION: Xaa is
              N-methyl-phenylalanine amide (xi)  SEQUENCE DESCRIPTION: SEQ ID NO 33

Xaa Gly Trp Leu Asp Xaa
  1               5

We claim:

1. A compound having the formula

Hpa(SO$_3$H)-Ahx-Gly-Trp-Ahx-MeAsp-Phe-NH$_2$ (SEQ ID NO 17) or a pharmaceutically acceptable derivative thereof.

\* \* \* \* \*